US006284242B1

(12) United States Patent
Kurachi

(10) Patent No.: US 6,284,242 B1
(45) Date of Patent: *Sep. 4, 2001

(54) METHOD FOR ENHANCING MYOBLAST MIGRATION AND INVASION IN THE CONTEXT OF GENE THERAPY

(75) Inventor: Kotoku Kurachi, Ann Arbor, MI (US)

(73) Assignee: Regents of the University of Michigan, Ann Arbor, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/293,125

(22) Filed: Apr. 16, 1999

(51) Int. Cl.$^7$ ............................ C12N 15/500; C12N 5/00; A61K 31/70; A01N 43/04
(52) U.S. Cl. ........................ 424/93.21; 435/325; 435/347; 435/455; 514/44
(58) Field of Search ................................ 424/93.1, 93.21; 435/320.1, 325, 455; 536/23.1; 514/44

(56) References Cited

U.S. PATENT DOCUMENTS 5,833,978 * 11/1998 Tremblay ............................ 424/93.7

OTHER PUBLICATIONS

Floyd et al, Gene Therapy 5(1):19–30, Jan. 1998.*
Yagamihiroomasa et al (Nature 377(6550):652–656, 1995.*
Tremblay et al, Basic and Applied Myology, 7(3–4):221–230, 1997.*
Anderson WF, Nature 392:25–30, 1998.*
Verma et al Nature 389:239–242, 1997.*
Touchette, Nat. Med. 2(1) 7–8, 1996.*
Guerette et al, Cell Trans. 6(2):101–107, 1997.*
Ohtsuka et al, J. Immunology 160(9):4635–4640, 1998.*
Floyd et al (Gene Therapy 5(1):19–30, 1998.*
Yagamihiroomasa et al (Nature 377(6550):652–656, 1995.*
Christ et al., "Experimental analysis of the origin of the wing musculature in avian embryos" *Anat. Embrylo.* 150:171–186 (1977).
Hughes and Blau, "Migration of myoblasts across basal lamina during skeletal muscle development" *Nature* 345:350–352 (1990).
Schultz et al., "Absence of exogenous satellite cell contribution to regeneration of frozen skeltal muscle" *J. Muscle Res. Cell Motil* 7:361–367 (1986).
Watt et al., "The movement of muscle precursor cells between adjacent regenerating muscles in the mouse" *Anat. Embryol.* 175:527–536 (1987).
Watt et al., "Migration of LacZ positive cells from the tibialis anterior to the extensor digitorum longus muscle of the X–linked muscular dystrophic (MDX) mouse" *J. Muscle Res. Cell Motil.* 14:121–132 (1993).

Watt et al., "Migration of muscle cells" *Nature* 368:496–407 (1994).
Moens et al. "Lack of myoblast migration between transplanted and host muscle of mdx and normal mice" *J. Muscle Res. Cell Motil.* 17:37–43 (1996).
Karpati et al., "Myoblast transfer in Duchenne muscular dystrophy" *Ann. Neurol* 34:8–17 (1993).
Morgan et al. "Normal myogenic cells from newborn mice restore normal histology to degenerating muscles of the mdx mouse" *J. Cell. Biol.* 111:2437–2449 (1990).
Yao and Kurachi, "Expression of human factor IX in mice after injection of genetically modified myoblasts" *Proc. Natl. Acad. Sci USA* 89:3357–3361 (1992).
Roman et al., "Circulating human or canine factor IX from retrovirally transduced primary myoblasts and established myoblast cell lines grafted into murine skeletal muscle" *Somatic Cell Mol. Genetics* 18:247–258 (1992).
Yao et al., "Primary myoblast–mediated gene transfer: presistent expression of human factor IX in mice" *Gene Therapy* 1:99–107 (1994).
Wang et al., "Persistant systematic production of human factor IX in mice by skeletal myoblast–mediated gene transfer: feasibility of repeat application to obtain therapeutic levels" *Blood* 90:1075–1082 (1997).
Yao and Kurachi, "Implanted myoblasts not only fuse with myofibers but also survive as muscle precursor cells" *J. Cell Sci.* 105:957–963 (1993).
Law et al., "Human gene therapy with myoblast transfer" *Transplant. Proc.* 29:2234–2237 (1990).
Huard et al., "Human myoblast transplantation: preliminary results of 4 cases" *Muscle & Nerve* 15:550–560 (1992).
Mendell et al., "Myoblast transfer in the treatment of Duchenne's muscular dystrophy" *New England J. Med.* 333:832–838 (1995).
Gussoni et al., "The fate of individual myoblasts after transplantation into muscles of DMD patients" *Nature Medicine* 3:970–977 (1997).
Huard et al., "The basal lamina is a physical barrier to herpes simplex virus–mediated gene delivery to mature muscle fibers" *J. Virol.* 70:8117–8123 (1996).
Wernig et al., "Formation of new muscle fibers and tumors after injection of cultured myogenic cells" *J. Neurocytol.* 20:982–997 (1991).

(List continued on next page.)

Primary Examiner—Deborah J. R. Clark
Assistant Examiner—Sumesh Kaushal
(74) Attorney, Agent, or Firm—Medlen & Carroll, LLP

(57) ABSTRACT

A novel, empirically derived composition of cytokines and myoblasts is described, that allows for the migration of myoblasts through connective barriers, along with methods employing the composition in the in vivo migration of myoblasts for therapeutic purposes and gene therapy, as well as methods for the identification of agents that are agonistic or antagonistic to myoblast migration in vitro or in vivo.

20 Claims, 11 Drawing Sheets

OTHER PUBLICATIONS

Bonham et al., "Prolonged expression of therapeutic levels of human granulocyte–stimulating factor in rats following gene transfer to skeletal muscle" *Human Gene Therapy* 7:1423–1429 (1996).

Stetler–Stevenson et al., "Extracellular matrix 6: Role of matrix metalloproteinase in tumor invasion and metastasis" *FASEB J.* 7:1434–1441 (1993).

Guerin and Hollan, "Synthesis and secretion of matrix–degrading metalloproteinases by human skeletal muscle satellite cells" *Devel. Dynamics* 202:91–99 (1995).

Kinoshita et al., "Pretreatment of myoblast cultures with basic fibroblast growth factor increases the efficacy of their transplantation in MDX mice" *Muscle Nerve* 18:834–841 (1995).

Collins et al., "Growth factors as survival factors: regulation of apoptosis" *Bioessays* 16:133–138 (1994).

Bischoff, "Chemotaxis of skeletal muscle satellite cells" *Devel. Dynamics* 208:505–515 (1997).

Reich et al., "Effects of inhibitors of plasminogen activator, serine proteinases and collagenase IV on the invasion of basement membrane by metastatic cells" *Cancer Research* 48:307–3312 (1988).

Strongin et al.; "Mechanism of cell surface activation of 72–kDa type IV collagenase" *J. Biol. Chem.* 270:5331–5338 (1995).

Corcoran et al., "MMP–2: Expression, activation and inhibition" *Enzyme Protein* 49:7–19 (1996).

Durko et al., "Suppression of basement membrane type IV collagen degradation and cell invasion in human melanoma cells expressing an antisense RNA for MMP–1" *Biochimica et Biophysica Acta* 1356:271–280 (1997).

Werb et al., "Signal transduction through the fibronectin receptor induces collagenase and stromelysin gene expression" *J. Cell Biol* 109:877–889 (1989).

Huhtala et al., "Cooperative signaling by $\alpha5\beta$ and $\alpha5\beta1$ integrins regulates metalloproteinase gene expression in fibroblasts adhering to fibronectin" *J Cell Biol* 129:867–879 (1995).

Gullberg et al., "Analysis of fibronectin and vitronectin receptors of human fetal skeletal muscle cells upon differentiation" *Exper Cell Res* 220:112–123 (1995).

Rando et al., "The fate of myoblasts following transplantation into mature muscle"0 *Exper Cell Res* 220:383–389 (1995).

Daston et al., "Pax–3 is necessary for migration, not differentiation, of limb muscle precursors in the mouse" *Development* 122:1017–1027 (1996).

Bladt et al., "Essential role for the c–met receptor in the migration of myogenic precursor cells into the limb bud" *Nature* 376:768–771 (1995).

Venkatsubramanian and Solursh, "Chemotactic behavior of myoblasts" *Devel Biol* 104:406–407 (1984).

Krenn et al., "Hyaluronic acid influences the migration of myoblasts within the avian embryo wing bud" *Am J Anat* 192:400–406 (1991).

Chin and Werb, "Matrix metalloproteinases regulate morphogenesis, migration and remodeling of epithelium, tongue skeletal muscle and cartilage in the mandibular arch" *Development* 124:1519–1530 (1997).

Albini et al., "A rapid in vitro assay for quantitating the invasive potential of tumor cells" *Cancer Res* 47:3239–3245 (1987).

Albini et al., "Inhibition of invasion, gelatinase activity, tumor take and metastasis of malignant cells by N–acetyl-cysteine" *Int. J. Cancer* 61:121–129 (1995).

Aimes et al., "Cloning of a 72dKa matrix metalloproteinase (gelatinase) from chicken embryo fibroblasts using gene family PCR: expression of the gelatinase increases upon malignant transformation" *Biochem. J.* 300:729–736 (1994).

Masure et al., "Mouse gelatinase B: cDNA cloning, regulation of expression and glycosylation in WEHI–3 macrophages and gene organization" *Eur. J. Biochem.* 218:129–141 (1997).

Chen et al., "Isolation and characterization of a 70–kDa metalloproteinase (gelatinase) that is elevated in Rous Sarcoma virus–transformed chicken embryo fibroblasts" *J. Biol. Chem.* 266:5113–5121, (1991).

Bilato et al., "Intracellular signaling pathways required for rat vascular smooth muscle cell migration" *J. Clin. Invest.* 96:1905–1915 (1995).

Ferrari et al., "Muscle regeneration by bone marrow–derived myogenic progenitors" *Science* 279:1528–1530 (1998).

Neumeyer et al., "Arterial delivery of myoblasts to skeletal muscle" *Neurol.* 42:2258–2262 (1992).

* cited by examiner

METHOD FOR ENHANCING MYOBLAST MIGRATION AND INVASION IN THE CONTEXT OF GENE THERAPY

This invention was made in part with government support under grant HL58713 from the National Institutes of Health. The government has certain rights in the invention.

FIELD OF THE INVENTION

This invention generally relates to a novel composition comprising myoblasts and growth factors. The growth factors may include, for example, basic fibroblast growth factor (bFGF) and fibronectin (FN). The invention also relates to a novel composition comprising myoblasts transfected with vectors expressing metalloproteases and growth factors. Additionally, the invention relates to the use of these compositions in assays for the identification of agents which are antagonistic or agonistic for myoblast migration either in vivo or in vitro. Furthermore, the invention relates to the use of these compositions for the treatment of degenerative muscle diseases. Further still, the invention relates to the therapeutic use of these compositions and methods in gene therapy.

BACKGROUND

The ability of myoblasts to migrate through connective tissue barriers has important implications for muscle development, muscle regeneration, and myoblast-mediated gene transfer. During embryonic development, myogenic precursor cells migrate out of the somites and into the developing limb buds to form the limb musculature (Christ et al. "Experimental analysis of the origin of the wing musculature in avian embryos" *Anat. Embrylo.* 150:171–186, 1977), and myoblasts retain the ability to traverse the myofiber basal lamina during postnatal development (Hughes and Blau "Migration of myoblasts across basal lamina during skeletal muscle development" *Nature* 345:350–352, 1990). A number of studies have also demonstrated migration of myoblasts both within (Schultz et al. "Absence of exogenous satellite cell contribution to regeneration of frozen skeletal muscle" *J. Muscle Res. Cell Motil* 7:361–367, 1986; Philips et al. "Migration of myogenic cells in the rat extensor digitorum longus muscle studied with a split autograft model" *Cell Tissue Res* 262:81–88, 1990) and between adult muscles (Watt et al. "The movement of muscle precursor cells between adjacent regenerating muscles in the mouse" *Anat. Embryol.* 175:527–536, 1987; Watt et al. "Migration of LacZ positive cells from the tibialis anterior to the extensor digitorum longus muscle of the X-linked muscular dystrophic (MDX) mouse" *J. Muscle Res. Cell Motil.* 14:121–132, 1993; Watt et al. "Migration of muscle cells" *Nature* 368:496–407, 1994; Moens et al. "Lack of myoblast migration between transplanted and host muscle of mdx and normal mice" *J. Muscle Res. Cell Motil.* 17:37–43, 1996). These studies have shown that in order to produce myoblast migration between muscles there must first be disruption of the thick outer epimysium on one or both muscles, combined with some sort of chemotactic stimulus or stimuli generated by conditions such as inflammation or regeneration of muscle.

In recent years, myoblast cell therapy and myoblast-mediated gene transfer therapy have been extensively explored for both muscle disorders, such as muscular dystrophy (Karpati et al. "Myoblast transfer in Duchenme muscular dystrophy" *Ann. Neurol* 34:8–17, 1993; Morgan et al. "Normal myogenic cells from newborn mice restore normal histology to degenerating muscles of the mdx mouse" *J. Cell. Biol* 111:2437–2449, 1990), and for disorders which require production of systemic protein factors such as factor IX (Yao and Kurachi "Expression of human factor IX in mice after injection of genetically modified myoblasts" *Proc. Natl. Acad. Sci USA* 89:3357–3361, 1992; Roman et al. "Circulating human or canine factor IX from retrovirally transduced primary myoblasts and established myoblast cell lines grafted into murine skeletal muscle" *Somatic Cell Mol. Genetics* 18:247–258, 1992; Yao et al. "Primary myoblast-mediated gene transfer: persistent expression of human factor IX in mice" *Gene Therapy* 1:99–107, 1994; Wane, et al. "Persistent systematic production of human factor IX in mice by skeletal myoblast-mediated gene transfer: feasibility of repeat application to obtain therapeutic levels" *Blood* 90:1075–1082, 1997). The implanted myoblasts not only fuse with the existing myofibers, but can also remain as satellite cells (Yao and Kurachi "Implanted myoblasts not only fuse with myofibers but also survive as muscle precursor cells" *J. Cell Sci.* 105:957–963, 1993), but in both cases these myoblasts must traverse the basal lamina. However, the results from clinical trials using myoblast cell therapy for Duchenne's muscular dystrophy (DMD) have been equivocal, with some reporting success (Law et al. "Human gene therapy with myoblast transfer" *Transplant. Proc.* 29:2234–2237, 1990; Huard et al. "Human myoblast transplantation: preliminary results of 4 cases" *Muscle & Nerve* 15:550–560, 1992) and others reporting less encouraging results (Karpati et al. "Myoblast transfer in Duchenne muscular dystrophy" *Ann. Neural.* 34:8–17, 1993; Mendell et al. "Myoblast transfer in the treatment of Duchenne's muscular dystrophy" *New England J. Med.* 333:832–838, 1995). It is evident from these studies that substantial improvements are needed before such therapies will become practical as a therapeutic intervention for human disorders.

One of the primary limiting factors in myoblast therapy is the overall efficiency of incorporation of myoblasts into the myofibers. Estimates have suggested that only 5–10% of the implanted myoblasts become incorporated and contribute to transgene expression (Gussoni et al. "The fate of individual myoblasts after transplantation into muscles of DMD patients" *Nature Medicine* 3:970–977, 1997; Wang et al "Persistent systemic production of human factor IX in mice by skeletal myoblast-mediated gene transfer: feasibility of repeat application to obtain therapeutic levels" *Blood* 90:1075–1082, 1997). Evidence from human clinical trials of myoblast implantation to correct DMD has suggested that even when the immune system is suppressed by cyclosporine treatment, myoblast incorporation into the host myofibers is still low, and only minimal long term effects were noted (Karpati et al. "Myoblast transfer in Duchenne muscular dystrophy" *Ann. Neurol.* 34:8–17, 1993). These studies suggested that another barrier to successful myoblast incorporation is the presence of connective tissue sheaths surrounding both fascicles and individual myofibers. Myoblasts must first traverse these barriers to access the myofiber surface in order to fuse with and incorporate into the myofiber syncytium. Moreover, human muscle contains thicker connective tissue sheaths than that of smaller organisms, and therefore this barrier may be even greater in humans than in experimental animal models such as mice. Thus the ability of myoblasts to cross connective tissue barriers may have a major effect on the overall efficiency of the gene transfer process. Recent studies have also demonstrated that the myofiber basal lamina is a significant barrier to viral-mediated in vivo gene transfer as well (Huard et al.

"The basal lamina is a physical barrier to herpes simplex virus-mediated gene delivery to mature muscle fibers" *J. Virol.* 70:8117–8123, 1996).

Physical and chemical disruption of the basal lamina by damaging the muscle would allow implanted myoblasts to cross the basal lamina and merge with the concomitant regeneration program, regenerating the muscle fibers with a mosaic of endogenous and implanted myonuclei. Most studies on myoblast transfer in animal models have used either physical injury (Wernig et al. "Formation of new muscle fibers and tumors after injection of cultured myogenic cells" *J. Neurocytol.* 20:982–997, 1991; Morgan et al. "Normal myogenic cells from newborn mice restore normal histology to degenerating muscles of the mdx mouse" *J. Cell Biol.* 111:2437–2449, 1990) or myotoxic agents (Salminen et al. "Implantation of recombinant rat myocytes into adult skeletal muscle: a potential gene therapy" *Human Gene Therapy* 2:15–26, 1991; Bonham et al. "Prolonged expression of therapeutic levels of human granulocyte-stimulating factor in rats following gene transfer to skeletal muscle" *Human Gene Therapy* 7:1423–1429, 1996) to produce this effect. However, these approaches may be too harmful and destructive for gene therapy in patients, particularly those suffering from disorders such as DMD or hemophilia.

Therefore, what is needed is a less destructive method for delivering genetically engineered therapeutics to muscles in the body.

SUMMARY OF THE INVENTION

The present invention generally relates to novel compositions comprising myoblasts and various growth factors. Additionally, the invention relates to novel compositions comprising myoblasts genetically engineered to express certain proteins (e.g. various metalloproteases (MMP) and various therapeutic proteins) and various growth factors. In one preferred embodiment the invention generally relates to novel compositions comprising myoblasts transfected with constructs expressing MMP-1 and MMP-2. In another embodiment, the invention relates to novel compositions comprising said transfected myoblasts and various growth factors. The selection of growth factors may include, but are not limited to, basic fibroblast growth factor (bFGF) and fibronectin (FN). Furthermore, the present invention relates to the use of said compositions to induce the migration of myoblasts and the invasion of myoblasts into myofibrils. Further still, the present invention relates to using said compositions to screen for agents that are agonistic or antagonistic to myoblast migration and invasion into myofibrils. Further still, the present invention relates to methods for treatment of degenerative muscular diseases and to delivery of therapeutic proteins by utilizing said transfected and untransfected myoblasts and growth factors.

In one embodiment, the present invention contemplates a composition, comprising myoblasts transfected with a gene encoding a metalloprotease. It is not intended that the present invention be limited to the degree of expression. However, it is preferred that the level of expression of the metalloprotease exceeds that of the untransfected myoblast. The present invention contemplates embodiments, wherein the gene is part of a vector which encodes at least one metalloprotease (i.e. vectors encoding more than one metalloprotease are contemplated—in addition, transfections with more than one vector, each comprising a gene encoding a metalloprotease is also contemplated).

In a preferred embodiment, said myoblasts have been co-transfected with a gene encoding a therapeutic gene product. Alternatively, two populations of myoblasts are mixed: one population transfected with the gene encoding the metalloprotease and the other population transfected with the gene encoding a therapeutic gene product.

The present invention also contemplates a host, said host comprising myoblasts transfected with a gene encoding a metalloprotease. Again, it is preferred that said myoblasts have been co-transfected with a gene encoding a therapeutic gene product. Again, multiple vectors and multiple metalloproteases are contemplates as well.

The present invention also contempaltes a method, comprising: a) providing i) transfected myoblasts, said transfected myoblasts transfected with a gene encoding a therapeutic gene product, ii) a host, and iii) fibroblast growth factor and fibronectin; b) culturing said transfected myoblasts in the presence of said fibroblast growth factor and said fibronectin to create cultured, transfected myoblasts; and c) introducing said cultured, transfected myoblasts into said host. The present invention contemplates variations on this embodiment, such as where said myoblasts have been co-transfected with a gene encoding a metalloprotease.

In one embodiment, myoblast migration assays are established, comprising: a) providing i) myoblasts from a donor, ii) one or more growth factors selected from the group consisting of bFGF and FN, iii) one or more compounds suspected of being agonistic or antagonistic to myoblast migration; b) culturing said myoblasts under conditions to measure cell migration, wherein migration of myoblasts is measured in the presence and absence of said one or more growth factors and compounds. The present invention contemplates using the above named compositions, and variations thereof, in screening assays for the detection of substances that are agonistic or antagonistic to myoblast invasion of myofibrils. High-throughput in vitro screening techniques are also contemplated in this invention.

In another embodiment, compounds suspected of inhibiting or promoting myoblast migration may be screened in vivo using, for example, mouse models, with the assay comprising: a) providing a host (e.g. a living animal); b) extracting myoblasts from said host; c) culturing said myoblasts with and without a compound suspected of being agonistic or antagonistic to myoblast migration so as to create a first and second preparation of cultured myoblasts; d) introducing at least a portion of said first and second preparations of cultured myoblasts into the said host under conditions such that the migration of said first and second preparations of said cultured myoblasts can be compared. In a preferred embodiment said cultured cells would be marked for easy identification after reintroduction into the host. Said means of identification would be known by those practiced in the art and may include transfection into said myoblasts of constructs that express a marker protein (e.g. green fluorescent protein (GFP), beta-galactosidase (β-gal), luciferase or an expression product (antigen) detectable with a specific antibody), incorporation into said myoblasts of radioactive markers and incorporation into said myoblasts of easily assayable marker proteins or chemicals. In another preferred embodiment said cultured cells would be transfected with constructs that express metalloproteases including, but not limited to, MMP-1, and MMP-2. Then said transfected myoblasts would be assayed as described herein above.

Furthermore, the present invention contemplates using the above named compositions, and variations thereof, to enhance the migration of myoblasts either in vivo or in vitro. In one embodiment, comprising, a) providing i) a patient, ii)

one or more growth factors selected from the group consisting of bFGF and FN, and iii) myoblasts (e.g. immunocompatible myoblasts) from a donor; b) contacting said myoblasts ex vivo with said growth factor under conditions to promote myoblast migration; and c) introducing said myoblasts into said patient.

While not limited to any mechanism, it is believed that, in part, culturing the cells in the manner proposed results in the expression by the cells of various metalloproteases, the expression of which permit the myoblasts to transverse the epimysium (connective tissue) surrounding the muscle. In this regard, the present invention provides a method of treatment of human muscular degenerative diseases (e.g. muscular dystrophy) comprising: a) providing a human patient diagnosed with a muscular degenerative disease; b) obtaining myoblasts from the patient or an immunocompatable donor; c) culturing said myoblasts in a culture medium, said culture medium comprising one or more of the above mentioned cytokines; and d) introducing at least a portion of said myoblasts into said patient so as to induce an in vivo therapeutic reaction. In another embodiment the method further comprises additional introductions or administrations of said myoblasts into said patient. The invention shall not be limited by the selection of cytokines used to promote migration of myoblasts and invasion by myoblasts into myofibrils.

In yet another embodiment, the invention comprises: a) providing i) myoblasts from a host and ii) a vector comprising MMP-1 and MMP-2 in an operable combination with a promoter; b) transfecting said myoblasts with said vector under conditions such that metalloproteases are expressed; c) culturing said transfected myoblasts with bFGF and FN so as to create treated transfected myoblasts, and; d) introducing at least a portion of said treated transfected myoblasts into said host.

Furthermore, the invention embodies the delivery of various therapeutic peptides via the introduction of genes into the myoblasts prior to the stimulation of the myoblasts with the cytokines that induce migration. One embodiment comprises: a) providing i) myoblasts obtained from the host and ii) a DNA vector which encodes the therapeutic peptide; b) transfecting said myoblasts with said vector to create transfected myoblasts; c) culturing said transfected myoblasts with bFGF and FN so as to create treated transfected myoblasts; and d) introducing at least a portion of said treated, transfected myoblasts into said host. In another embodiment, the method further comprises additional introductions of the said myoblasts into said patient. The invention shall not be limited by the selection of cytokines used to promote migration of myoblasts and invasion by myoblasts into myofibrils. In yet another embodiment, the invention comprises: a) providing i) myoblasts from a host and ii) a first vector which encodes a therapeutic peptide, and iii) a second vector that encodes a metalloproteases (e.g. MMP-1 and MMP-2); b) transfecting said myoblasts with said first and second vectors; c) culturing said transfected myoblasts with bFGF and FN so as to create treated, transfected myoblasts, and; d) introducing at least a portion of said treated transfected myoblasts into said host.

For culturing, the bFGF may be used at concentrations in a range from about 0.1 to 10 $\mu$g/ml bFGF. Likewise, the FN may be used at concentrations in a range from about 5 $\mu$g/ml to 500 $\mu$g/ml. In one embodiment, the culture medium contains bFGF at 1 $\mu$g/ml and FN at 50 $\mu$g/ml.

In other embodiments, said transfected and cultured cells may be cryogenically stored by methods known to those practiced in the art for later use in screening assays or for therapeutic purposes.

DEFINITIONS

Figure 1:
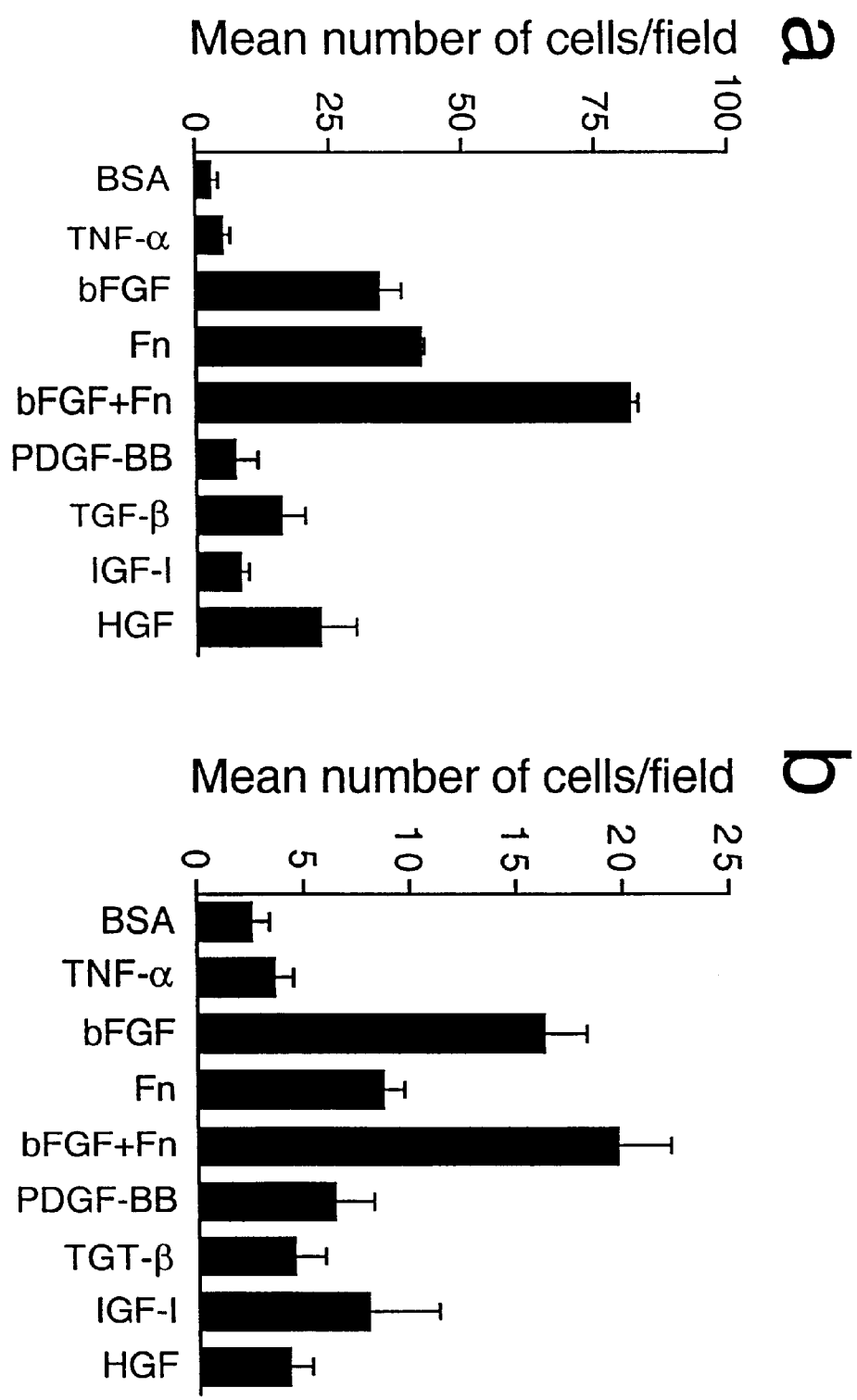
FIG. 1 shows the effect of growth factor and fibronectin stimulation of mouse myoblast migration and invasion in vitro. Panel a, mouse myoblast migration at 12 hours; panel b, mouse myoblast invasion at 24 hours.

To facilitate understanding of the invention, a number of terms are defined below.

As used herein, the term "purified" or "to purify" refers to the removal of contaminants from a sample. The present invention contemplates purified compositions (discussed above).

As used herein, the term "substantially purified" refers to the removal of a portion of the contaminants of a sample to the extent that the substance of interest is recognizable as the dominant species (in amount) by techniques known to those skilled in the art.

As used herein, the term "portion" when used in reference to a protein (as in "a portion of a given protein") refers to fragments of that protein. The fragments may range in size from four amino acid residues to the entire amino acid sequence minus one amino acid.

As used herein the term "portion" when in reference to cells (as in "a portion of the cells") refers to any amount less than the total number of cells available.

"Staining" shall be defined as any number of processes known to those in the field that are used to better visualize, distinguish or identify a specific component(s) and/or feature(s) of a cell or cells.

"Antibody" shall be defined as a glycoprotein produced by B cells that binds with high specificity to the agent (usually, but not always, a peptide), or a structurally similar agent, that generated its production. Antibodies may be produced by any of the known methodologies [Current Protocols in Immunology (1998) John Wiley and Sons, Inc., N.Y.] and may be either polyclonal or monoclonal.

"Antigen" shall be defined as a protein, glycoprotein, lipoprotein, lipid or other substance that is reactive with an antibody specific for a portion of the molecule.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g. a fluorescent microscope). Said antigen may be the product of a transfected expression vector.

"Morphology" shall be defined as the visual appearance of a cell or organism when viewed with the eye, a light microscope, a confocal microscope or an electronmicroscope, as appropriate.

"Patient" shall be defined as a human or other animal, such as a guinea pig or mouse and the like, capable of donating and receiving myoblasts.

"Myoblast" shall be defined as an muscle cell that has not fused with other myoblasts to form a myofibril and has not fused with an existing myofibril.

"Metalloprotease (MMP)" shall be defined as a member of a group of proteases that are capable of degrading various extracellular matrix and connective tissue proteins (e.g. collagens and proteoglycans).

"Vector" shall be defined as a circular double-strand DNA molecule capable of having any genes therein encoded transcribed when put into the appropriate environment in vivo or in vitro.

"Expression" shall be defined as the transcription and translation of a gene. Such transcription and translation may be in vivo or in vitro.

"Constitutive" shall be defined as the level of expression of a genomic gene in vivo.

"Overexpression" shall be defined as expression at a level above the level normally expressed by an untransfected cell and is reflected by the combined expression level of a genomic gene along with a similar gene transfected into a cell.

"Transfect" shall be defined as the introduction of a vector into a cell by means such as, e.g., eletroporation of lipofectamine.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

A "gene encoding a therapeutic gene product" is a gene that encodes a product having a therapeutic benefit. It is not intended that the present invention be limited to any particular therapeutic gene product. A variety of such genes and gene products are contemplated, including but not limited to, a gene encoding dystrophin. Dystrophin is therapeutic, for example, in dystrophin-deficient recipients. This, of course is not to say that the present invention only contemplates the dystrophin gene. For example, the gene may encode coagulation factors, (such as Factor IX), enzymes involved in specific metabolic defects, (such as urea cycle enzymes, especially ornithine transcarbamylase, argininosuccinate synthase, and carbamyl phosphate synthase); receptors, (e.g., LDL receptor); membrane transporters (e.g., glucose transporter); and a variety of cytoskeletal proteins. The gene may be of synthetic, cDNA or genomic origin, or a combination thereof. The gene may be one which occurs in nature, a non-naturally occurring gene which nonetheless encodes a naturally occurring polypeptide, or a gene which encodes a recognizable mutant of such a polypeptide. The present invention contemplates that such genes can be used with success with a variety of animals. Particular therapeutic success is achieved with humans.

GENERAL DESCRIPTION OF THE INVENTION

Research has demonstrated a central role for matrix metalloproteinases (MMPs) in cell migration and invasion, particularly during tumor metastasis (Stetler-Stevenson et al. "Extracellular matrix 6: Role of matrix metalloproteinases in tumor invasion and metastasis" *FASEB J.* 7:1434–1441, 1993). Human myoblasts have been shown to constitutively secrete MMP-2 (Guerin and Holland "Synthesis and secretion of matrix-degrading metalloproteinases by human skeletal muscle satellite cells" *Devel. Dynamics* 202:91–99, 1995), but currently there is only limited knowledge available on the basic biology underlying the fate of implanted myoblasts, the importance of MMPs and their relationship to physiological stimuli in myoblast migration and invasion in vitro and in vivo.

The present invention would utilize the endogenous physiological ability of cells to cross protein barriers. In this regard, the present invention pertains to novel compositions and methods for the enhancement of myoblast migration both in vitro and in vivo. The development of these compositions and methods allows for the screening and testing of compounds that are suspected of being agonistic or antagonistic for myoblast migration. Additionally, the present invention pertains to the delivery of therapeutic proteins by introduction into patients of myoblasts that were transfected with a vector encoding the therapeutic protein and then cultured by the methods of the present invention. Furthermore, the invention pertains to the treatment of degenerative muscle diseases.

A. Cytokines and Growth Factors in Myoblast Migration

Gene therapy is emerging as a powerful tool in the development of new treatments for hereto untreatable diseases. In this regard, the present invention relates to compositions and methodologies needed for the advancement of therapeutic intervention in muscular degenerative diseases. We previously reported that treatment of skeletal myoblasts with certain growth factors, particularly bFGF, substantially increases myoblast-mediated factor IX gene transfer in mice (Yao et al. "Primary myoblast-mediated gene transfer: persistent expressing of human factor IX in mice" *Gene Therapy* 1:99–107, 1994), and similar effects of bFGF were also described for myoblast cell therapy (Kinoshita et al. "Pretreatment of myoblast cultures with basic fibroblast growth factor increases the efficacy of their transplantation in MDX mice" *Muscle Nerve* 18:834–841, 1995). However, the ability of bFGF to be of any use in modulating the migration and transplantation of myoblasts has remained unclear. The present invention pertains to the use of various growth factors (e.g. bFGF and FN) in vitro and in vivo in regards to their ability to induce myoblast migration and invasion and greatly enhance myoblast transplantation.

The growth factors tested here are known to have significant effects on proliferation, differentiation or survival of myoblasts (Collins et al. "Growth factors as survival factors: regulation of apoptosis" *Bioessays* 16:133–138, 1994). Growth factors such as PDGF-BB and bFGF strongly stimulate myoblast proliferation and suppress differentiation, while others such as TGF-β suppress proliferation. Their effect on myoblast migration and invasion is much less well understood. It is possible that these growth factors may effect myoblast migration and invasion (FIG. 1) through enhancing cell proliferation and survival, as suggested in the literature. However, the major effects of growth factors on cell migration and invasion observed in the present studies can not be completely due to such activities because the duration of the in vitro assay is too short to produce significant effects on cell proliferation and/or differentiation.

B. Effect of Growth Factors in Murine Myoblast Migration

Among the growth factors tested with mouse myoblasts, bFGF reproducibly showed the strongest stimulatory effects on mouse myoblast migration and invasion in vitro (FIG. 1). This agrees with the importance of bFGF in migration in murine myoblasts, though no significant effects of bFGF were reported on rat myoblast migration (Bischoff "Chemotaxis of skeletal muscle satellite cells" *Devel. Dynamics* 208:505–515, 1997). This suggests possible species differences of bFGF effects on myoblasts. The different effects of bFGF and other growth factors observed with mouse and human cells in the present studies also agree with such species differences. These combined results demonstrate the unpredictable nature of the effect of these factors on the migration and invasion of myoblasts from different species prior to actual testing.

Figure 2:
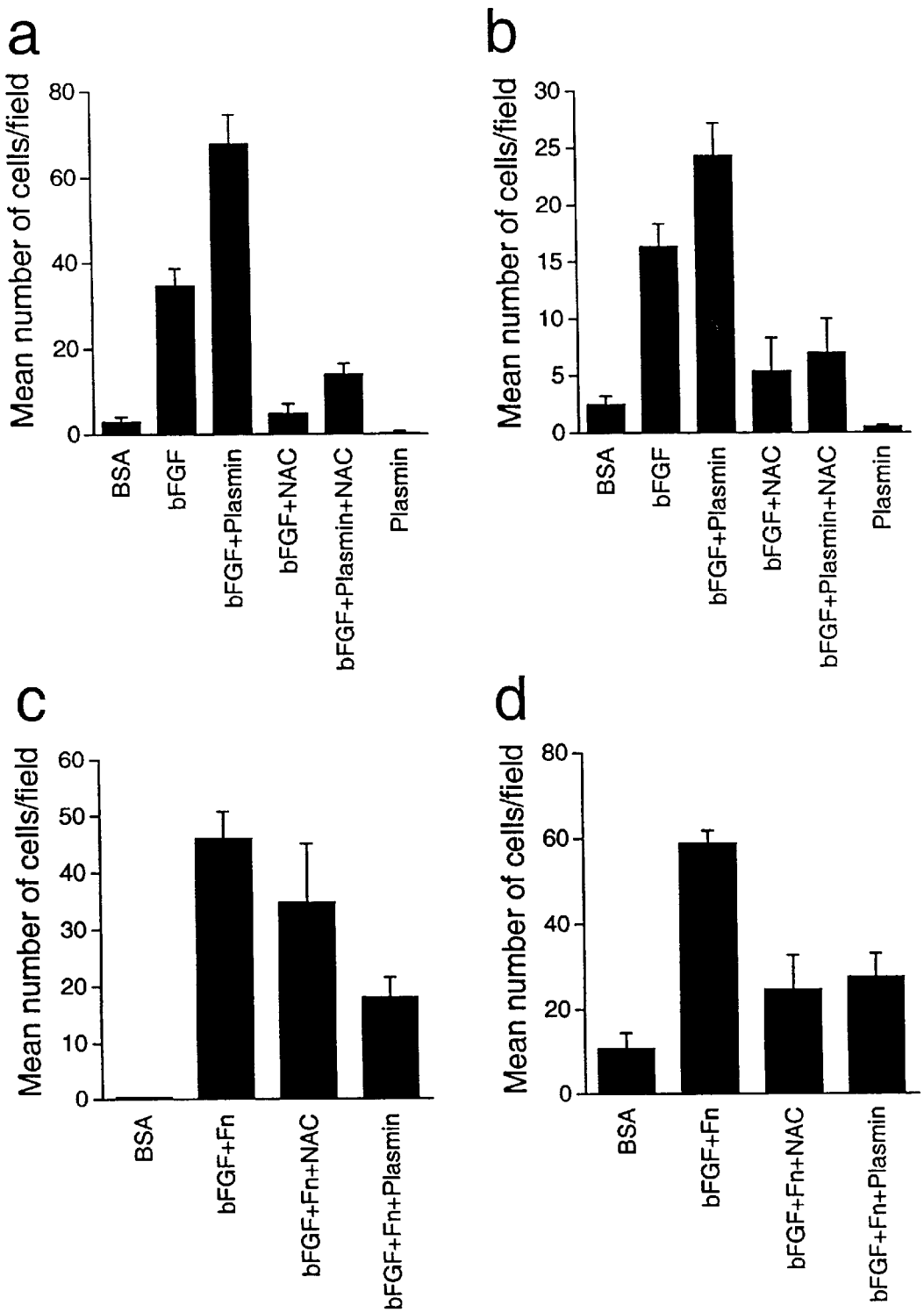
FIG. 2 shows the migration and invasion of mouse myoblasts in response to MMP activators and inhibitors. Panels a and c, mouse myoblast migration assays with various stimulants as labeled; panels b and d, mouse myoblast invasion assays with various stimulants as labeled at. Migration and invasion were assayed at 12 and 24 hours, respectively.
Figure 7:
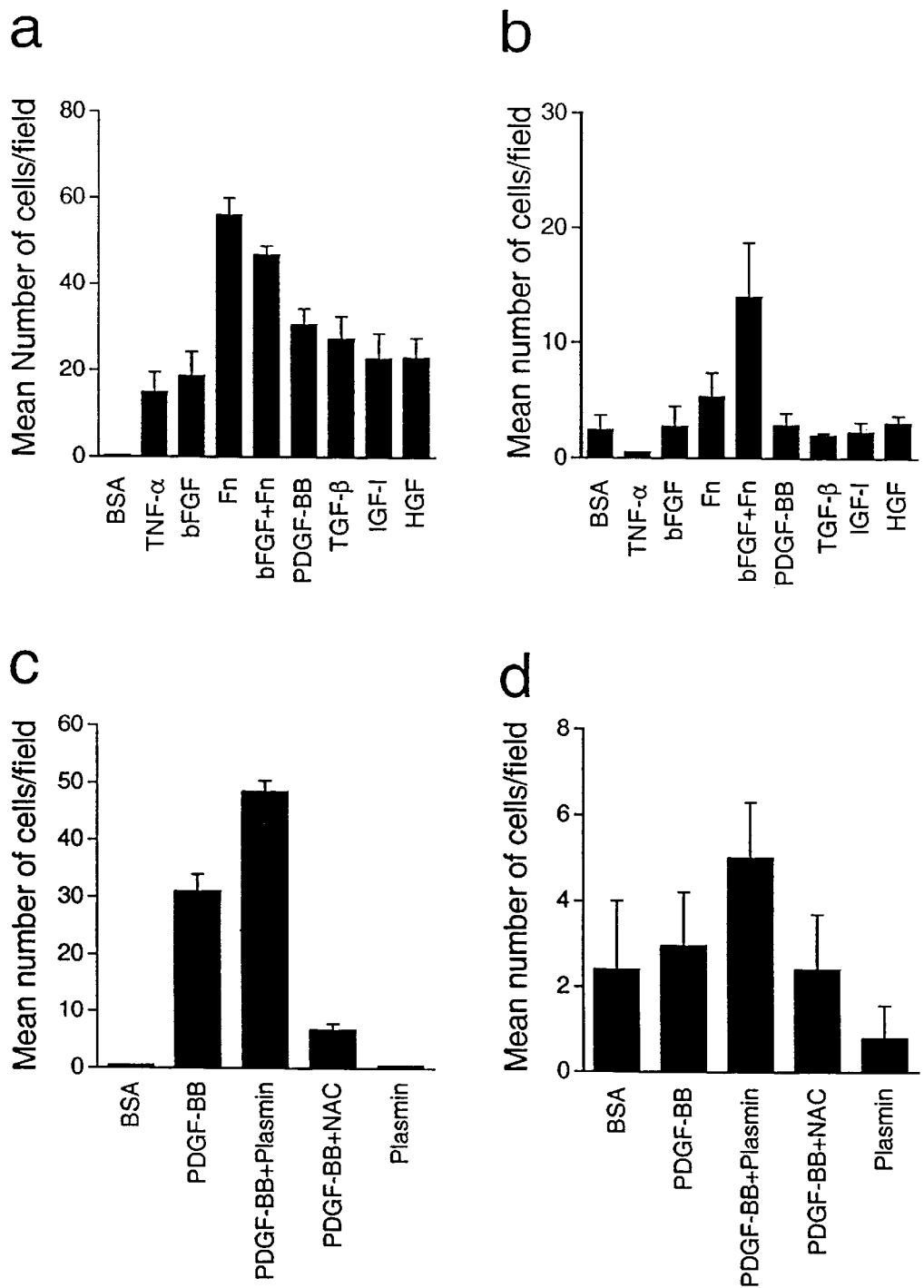
FIG. 7 shows the migration and invasion of human myoblasts in response to growth factors and fibronectin in vitro. Panel a, effects on migration (12 hours); panel b, effects on invasion (24 hours); panel c, effects of plasmin and N-acetyl cysteine (NAC) on migration induced by PDGF-BB; panel d, effects of plasmin and NAC on invasion induced by PDGF-BB. Bars represent mean±SEM of at least three separate experiments.

In addition to bFGF, fibronectin also has strong augmenting effects on both migration and invasion of mouse myoblasts. It is important to note that the combination of bFGF and fibronectin has an additive stimulatory effect on mouse myoblast migration and invasion (FIG. 1). This strong effect may be due to 1) an induction of greater MMP-2 expression compared with bFGF alone (bFGF also induces low level activation of MMP-2 and a moderate level MMP-9 expression), and 2) induction and activation of MMP-2 by fibronectin. Together, these results support the critical role of MMP-2 in these cell processes. This is further supported by the MMP-2 over-expression experiment, which showed that the elevated MMP-2 expression substantially increases the migration and invasion capacity of myoblasts, while N-acetyl cycteine (NAC) effectively suppressed the effects (FIG. 7). The importance of the activated form of MMP-2 for migration and invasion of mouse myoblasts is also supported by the substantial enhancement of bFGF effects by plasmin treatment, which proteolytically activates MMPs, (Reich et al. "Effects of inhibitors of plasminogen activator, serine proteinases and collagenase IV on the invasion of basement membrane by metastatic cells" *Cancer Research* 48:307–3312, 1988), and also by substantial suppression of positive bFGF effects by N-acetyl cysteine (NAC) (FIG. 2). MMP-2 can also be activated by MT-MMP, a cell-membrane bound MMP (Strongin et al. "Mechanism of cell surface activation of 72-kDa type IV collagenase" *J. Biol. Chem.*270:5331–5338, 1995). Therefore, the effects of growth factors and fibronectin on MMP-2 may also be conferred via their effects on MT-MMP. Activated MMP-2 has also been implicated in tumor cell invasion and metastatic potential (Deryugina et al. "Tumor cell invasion through Matrigel® is regulated by activated matrix metalloproteinase-2" *Anticancer Res.* 17:3201–3210, 1997; Corcoran et al. "MMP-2: Expression, activation and inhibition" *Enzyme Protein* 49:7–19, 1996).

Although none of the reagents tested in the present studies had any noticeable effects on MMP-1 expression, transient over-expression of MMP-1 produced an increase, almost equivalent to that of MMP-2, in the migration and invasion of mouse myoblasts (FIG. 7). Such activities are also substantially suppressed by NAC. MMP-1 has been implicated in the invasion of other cells including tumor cells (Durko et al. "Suppression of basement membrane type IV collagen degradation and cell invasion in human melanoma cells expressing an antisense RNA for MMP-1" *Biochimica et Biophysica Acta* 1356:271–280, 1997). Interestingly, co-transfection of MMP-1 and MMP-2 is less effective than transfection with each MMP alone, suggesting that their mechanisms of action are moderately competitive in the nature, rather than neutral or synergistic.

Figure 4:
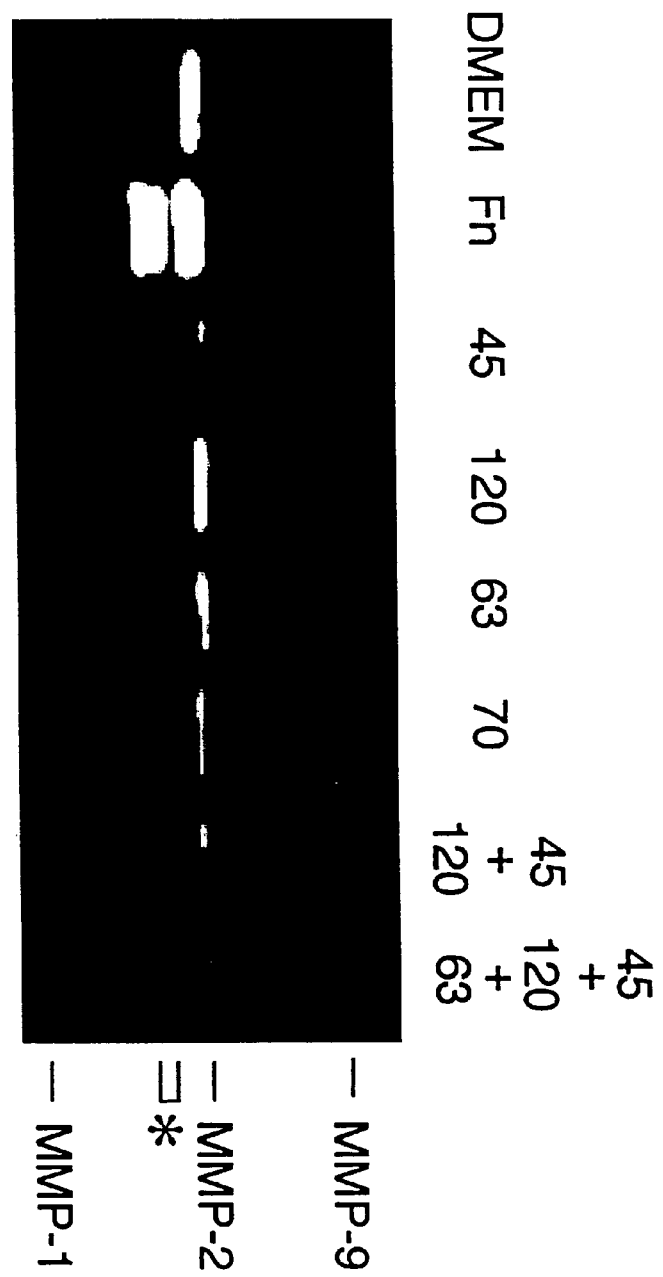
FIG. 4 shows a gelatin zymography showing effects of fibronectin fragments on MMP-2 activation.
Figure 5:
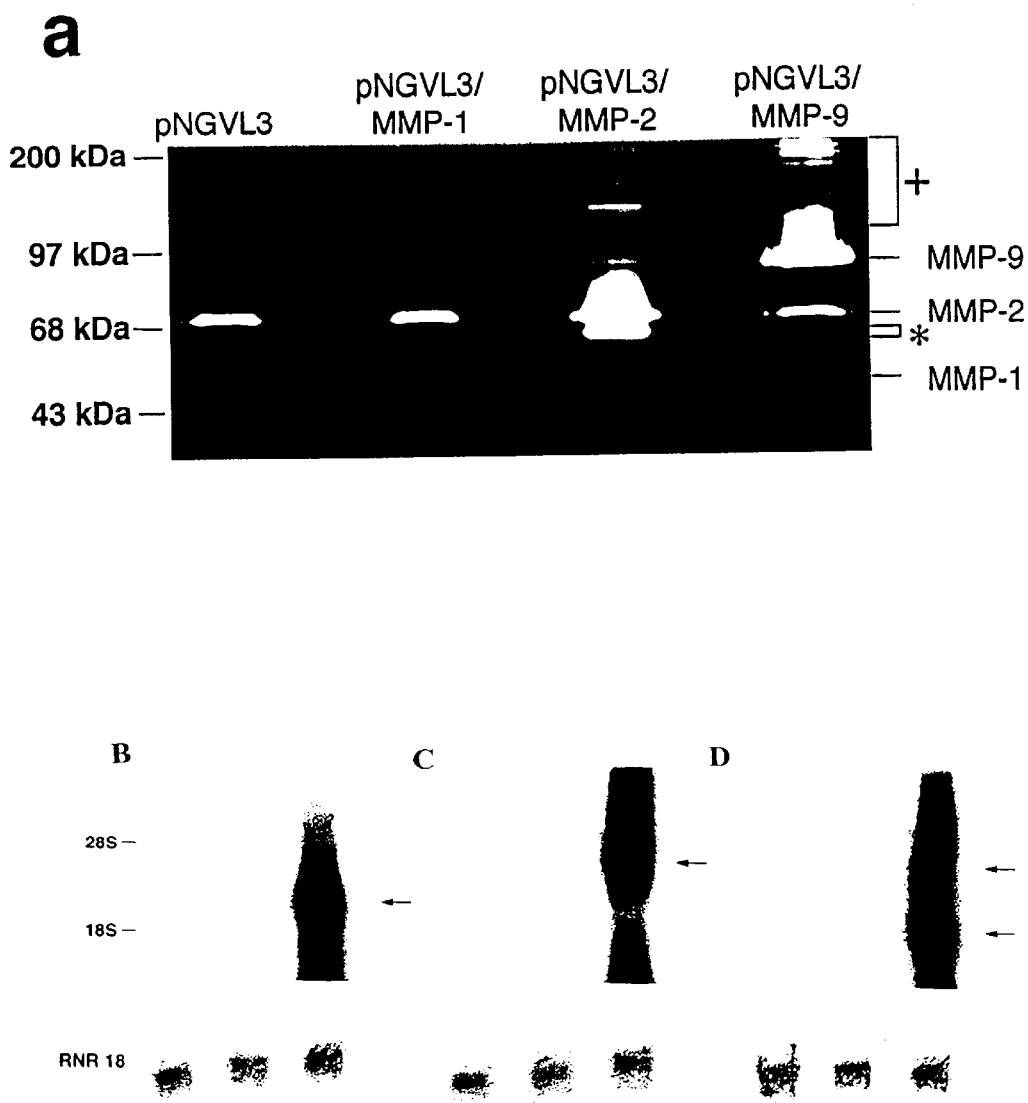
FIG. 5 shows MMP over-expression. Panel a, gelatin zymogram of myoblasts transiently transfected with expression vectors for human MMP-1, MMP-2, or MMP-9. Panels b, c and d show Northern blot analysis.

The minimal role of MMP-9 in murine myoblast migration and invasion is demonstrated by the marginal effects of TNF-α, which can strongly induce MMP-9 expression and only negligibly increased MMP-2 expression (FIG. 4). This is supported by the lack of an effect of over-expression of MMP-9 on myoblast migration and invasion (FIG. 5). However, the possibility that MMP-9 may induce or suppress myoblast migration and/or invasion through cooperation with other as-yet unidentified factors or conditions remains to be tested. Since bFGF, which strongly stimulates both migration and invasion of mouse myoblasts, can also increase MMP-9 expression in addition to its effects on MMP-2, MMP-9 apparently does not function to override the positive effects of MMP-2 on migration and invasion.

Figure 6:
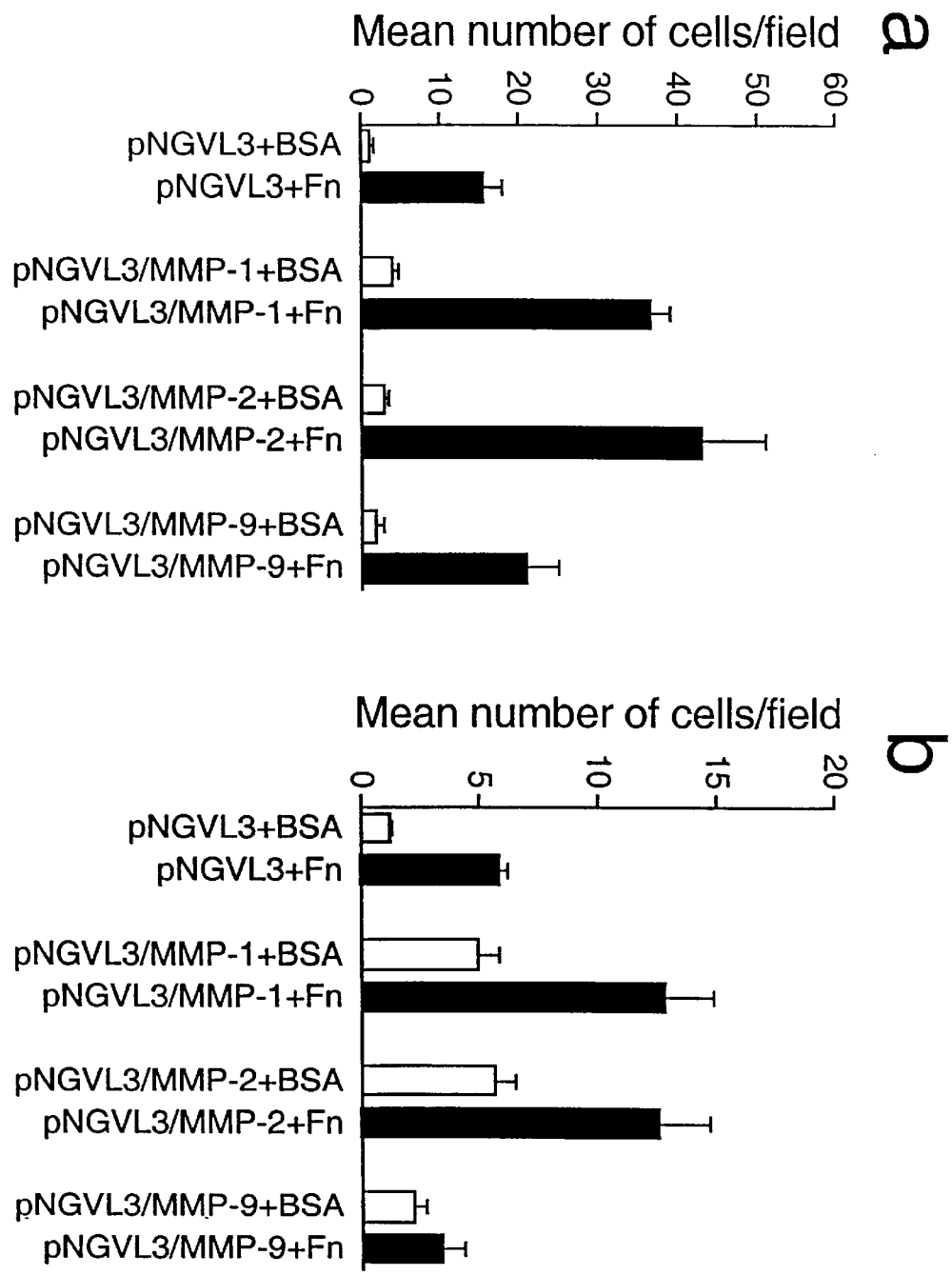
FIG. 6 shows the effects of overexpressed MMP-1, -2 and -9 on migration and invasion of mouse myoblasts. Panel a, effects on migration. Panel b, invasion of mouse myoblasts transfected MMP expression vectors. Bars represent mean±SEM from three individual experiments.

Together, these data indicate that the increased expression and activation of MMP-2 or MMP-1, but not of MMP-9, play a critical role in migration and invasion of myoblasts. Although this is one of the important conclusions obtained in the present studies, it is important to note that the increased expression and activation of MMP-2 alone does not account for all of the results observed. Regardless of the absence or presence of plasmin, migration and invasion of the control myoblasts (treated only with BSA), which constitutively express a substantial level of MMP-2 (FIG. 3) (Guerin and Hollard "Synthesis and secretion of matrix-degrading metalloproteinases by human sketal muscle satellite cells" *Devel. Dynamics* 202:91–99, 1995), was minimal. regardless of the absence or presence of plasmin, migration and invasion of the control Furthermore, bFGF has only a moderate effect on the MMP-2 expression level, yet it has substantial effects on mouse myoblast migration and invasion. These results suggest that myoblast migration and invasion require some other, as yet unidentified factor(s) in addition to MMP-2 and MMP-1. This notion is consistent with the results obtained from the MMP over-expression experiments, where a low dose of fibronectin is needed to prime cell migration to amplify the effects of over-expressed MMPs (FIG. 6). Without this directional priming, MMP over-expression alone gives only a small increase in migration and invasion over the basal control levels. It is therefore necessary to point out that the combination of elements that we have deduced is novel and unexpected.

C. Effect of Growth Factors in Human Myoblast Migration

Human myoblasts responded to growth factor treatment differently from mouse myoblasts. Treatment of human myoblasts with any growth factors, including TNF-α and bFGF, had no appreciative effects on MMP-1, MMP-2 or MMP-9 expression. The high basal level of MMP-2 expression of human cells may make them less sensitive to additional treatment with these growth factors, which primarily function to increase MMP-2 expression. This is further supported by the observation that fibronectin induces significant activation of MMP-2, and increases its effects on migration of human myoblasts (FIG. 7a). Interestingly, the effect of fibronectin alone on human myoblast invasion is small, but together with bFGF, its effect is synergistic increasing to several fold higher than the BSA control level. These results indicate that the factors and conditions which affect migration and invasion of human myoblasts are somewhat different from those of mouse cells. Human myoblasts have a great potential for migration, presumably due to the high constitutive MMP-2 expression, though an appropriate priming stimulus by treatment with growth factors or fibronectin is still needed for cells to initiate migration (FIG. 7a). Invasion of human myoblasts across MATRIGEL® is less than mouse cells (FIG. 7b). The differences observed between mouse and human cells appear not to be dependent on the age of the individual from which cells were isolated, as myoblasts from individuals 44 and 8 years old behaved similarly (data not shown).

D. Effect of Growth Factors on Metalloprotease Expression

It is noteworthy that soluble fibronectin, but not the substrate-bound fibronectin, can substantially increase MMP-2 expression and induce proteolytic activation of MMP-2 in both mouse and human myoblasts. Fibronectin, however, does not significantly affect the expression levels of MMP-1 and MMP-9. Interestingly, fibronectin sub-fragments which contain critical binding sites for integrins, heparin and collagen, were unable either alone or in combination to elevate MMP-2 expression and activation in mouse myoblasts any significantly (FIG. 5). Similarly, these fibronectin sub-fragments were also unable to increase migration and invasion of mouse cells any significantly (data not shown). This is also consistent with the observation that the strong stimulatory effects of fibronectin in combination with bFGF or MMP over-expression is almost completely abolished by addition of plasmin, presumably due to fragmentation of fibronectin. This suggests that the fibronectin signal transduction pathway leading to the elevated MMP-2 expression and activation may require the small amino terminal distal portion of the molecule, which is the only part of fibronectin absent in these fragments. Alternatively, the structures responsible for MMP-2 activation may be required to be on the same molecule, but not supplied in trans by separate molecules. Yet another possibility is that the selection of fragments that we used were not of the proper length nor of the proper segment to activate MMP-2 expression.

Fibronectin regulation of migration, invasion and MMP expression has been demonstrated for other cell types (Akiyama et al. "Fibronectin and integrins in invasion and metastasis" *Cancer Met Rev* 14:173–189, 1995). Werb et al. ("Signal transduction through the fibronectin receptor induces collagenase and stromelysin gene expression" *J. Cell Biol* 109:877–889, 1989) reported that plating of rabbit synovial fibroblasts on fragments of fibronectin which interact with the α5β1 integrin, induce collagenase (MMP-1) expression, while fragments which interact with (α4β1 integrin suppresses MMP-1 expression. Intact fibronectin, which contains both domains, had no significant effect on MMP-1 expression (Werb et al. "Signal transduction through the fibronectin receptor induces collagenase and stromelysin gene expression" *J. Cell Biol* 109:877–889, 1989; Huhtala et al. "Cooperative signaling by α5β and α5β1 integrins regulates metalloproteinase gene expression in fibroblasts adhering to fibronectin" *J Cell Biol* 129:867–879, 1995). Since proliferating myoblasts express α5β1 (Gullberg et al. "Analysis of fibronectin and vitronectin receptors on human fetal skeletal muscle cells upon differentiation" *Exper Cell Res* 220:112–123, 1995), but not α4β1 integrin (Rosen et al. "Roles for the integrin VLA-4 and its counter receptor VCAM-1 in myogenesis" *Cell* 69:1107–1119, 1992), fibronectin would have inductive, but not suppressive effects on MMP-1. The lack of an increase in MMP-1 expression in response to fibronectin observed in the present studies may suggest the existence of cell type-specific and/or species-specific differences between fibroblasts and myoblasts in integrin-mediated regulation of MMP expression.

E. In vivo Implantation of Murine Myoblasts

Figure 9:
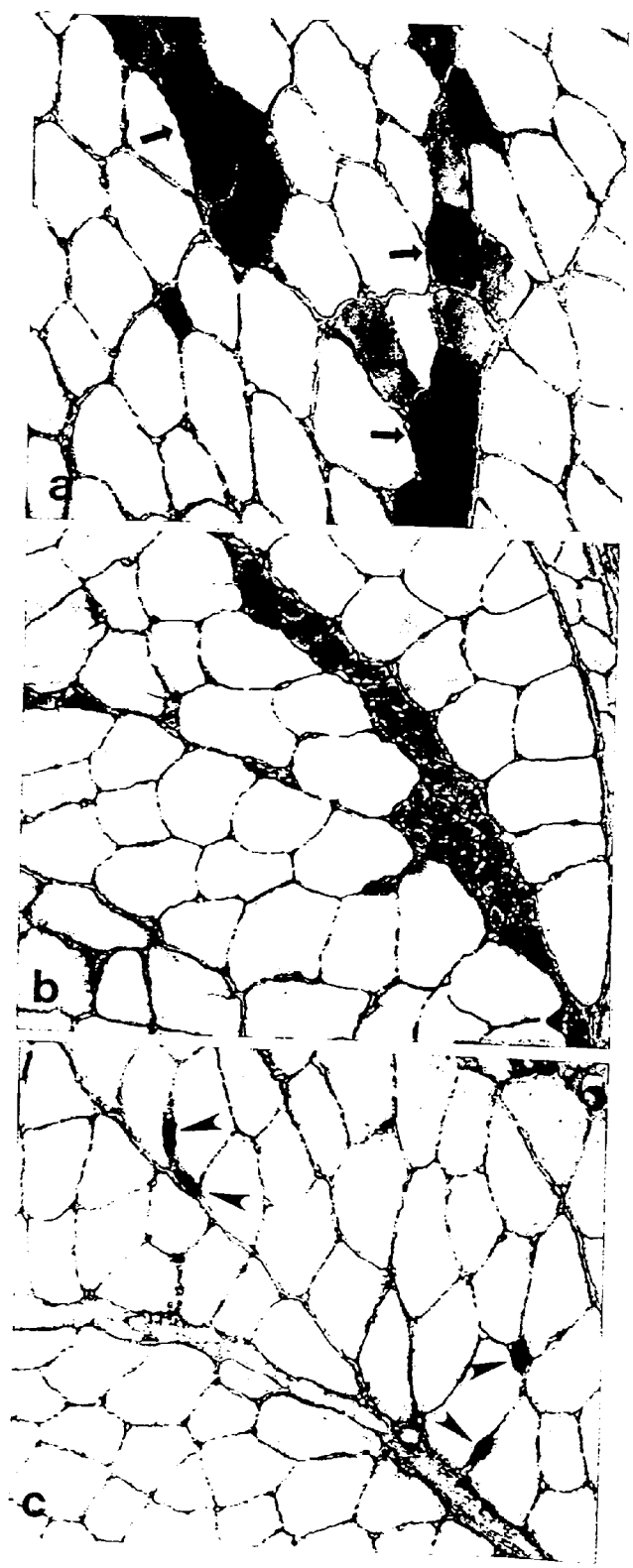
FIG. 9 shows histochemical analyses of transverse sections of SCID mouse muscles implanted with myoblasts carry β-galactosides expression vector (BAG).
Figure 10:
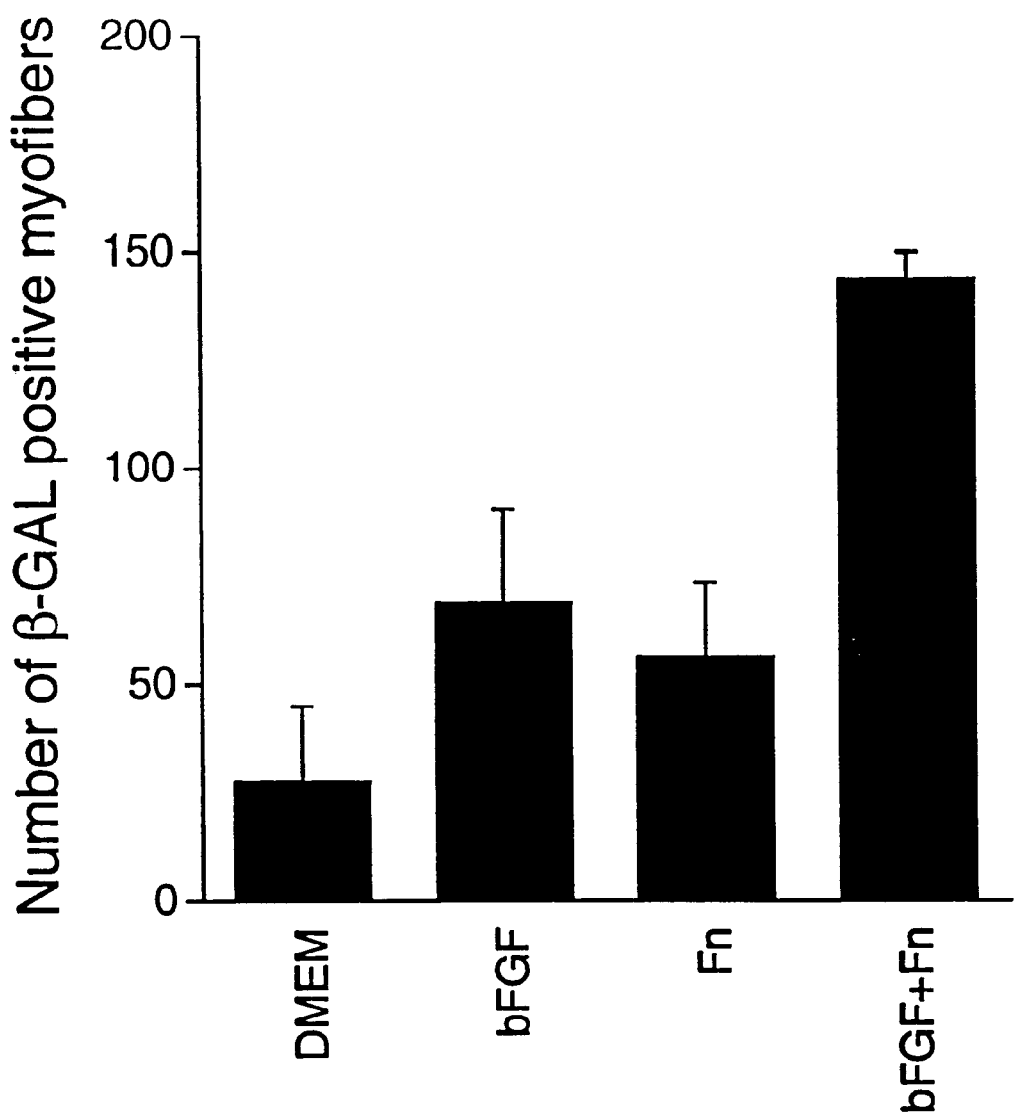
FIG. 10 shows the effects of bFGF and fibronectin on myoblast incorporation in vivo.
Figure 11:
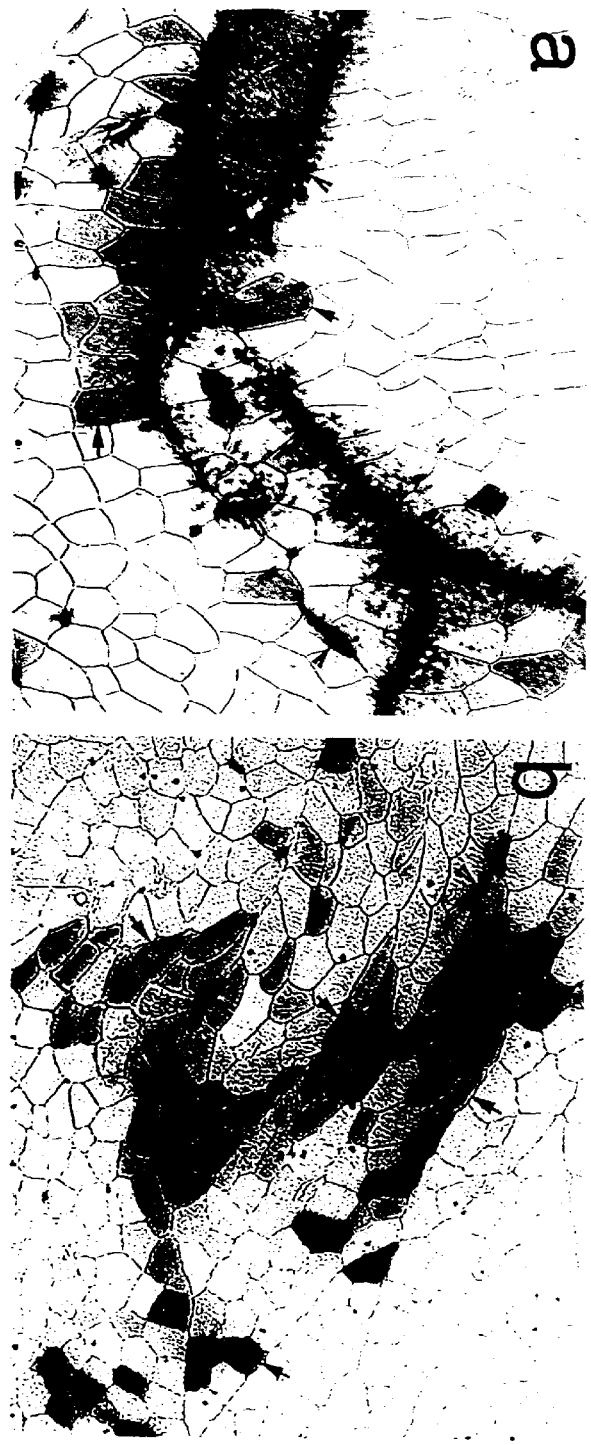
FIG. 11 shows the effects of bFGF and fibronectin on myoblast-mediated β-GAL gene transfer in vivo. Panel a, myoblasts treated with DMEM alone (control); panel b, myoblasts treated with a combination of bFGF and fibronectin.

When implanted intramuscularly (I.M.) in mice, myoblasts can fuse with the host myofiber cells (FIG. 9a), as has been described (Yao and Kurachi "Expression of human factor IX in mice with myoblasts but also survive as muscle precursor cells" *Proc Natl Acad Sci USA* 89:3357–3361, 1992; Yao and Kurachi "Implanted myoblasts not only fuse with myoblasts but also survive as muscle precursor cells" *J Cell Sci* 105:957–963, 1993; Yao et al. "Primary myoblast-mediated gene transfer: persistent expression of human factor IX in mice" *Gene Therapy* 1:99–107, 1994; Rando et al. "The fate of myoblasts following transplantation into mature muscle" *Exper Cell Res* 220:383–389, 1995; Wang et al. "Persistent systemic production of human factor IX in mice by skeletal myoblast-mediated gene transfer: feasibility of repeat application to obtain therapeutic levels" *Blood* 90:1075–1082, 1997). However, the efficiency of incorporation is poor and only a small fraction of the implanted cells actually participate in transgene expression as mentioned above (Gussoni et al. "The fate of individual myoblasts after transplantation into muscles of DMD patients" *Nature Medicine* 3:970–977, 1997; Wang et al. "Persistent systemic production of human factor IX in mice by skeletal myoblast-mediated gene transfer: feasibility of repeat application to obtain therapeutic levels" *Blood* 90:1075–1082, 1997). A substantial fraction of implanted myoblasts actually remain trapped within the connective tissues, and unable to cross basal lamina to fuse with myofibers. These myoblasts form new myotubes in the connective tissue (FIG. 9b,c). Whether or not these newly formed myotubes within the connective tissues can eventually mature, become innervated and form an integral part of muscle tissue is not known, and must be determined. However, by pre-treating cells with bFGF, fibronectin or with both, before implantation, a substantial increase in incorporation of the implanted myoblasts into the existing host myofiber cells can be achieved (FIG. 10). This is observed in tissue sections prepared from the muscle tissue injected either with the myoblasts treated with medium (control) or pre-treated with bFGF and fibronectin (FIGS. 11a and b, respectively). The former tissue contains a large number of newly formed myotubes (β-GAL positive) present within the connective tissues, while the latter contains a large number of β-GAL positive myofiber cells with fewer β-GAL positive myotubes trapped in the connective tissues.

F. Myoblast Mediated Gene Therapy

Together, these findings strongly suggest that a refined myoblast implantation procedure should be utilized to develop efficient and practical myoblast cell therapy and myoblast-mediated gene transfer. It is also noteworthy that characteristics of myoblast migration and invasion observed in response to bFGF, PDGF, HGF, fibronectin and MMP-2 are consistent with those described for migration of myogenic precursor cells during development (Daston et al. "Pax-3 is necessary for migration, not differentiation, of limb muscle precursors in the mouse" *Development* 122:1017–1027, 1996; Bladt et al. "Essential role for the c-met receptor in the migration of myogenic precursor cells into the limb bud" *Nature* 376:768–771, 1995; Venkatsubramanian and Solursh "Chemotactic behavior of myoblasts" *Devel Biol* 104:406–407, 1984; Krenn et al. "Hyaluronic acid influences the migration of myoblasts within the avian embryo wing bud" *Am J Anat* 192:400–406, 1991; Brand-Saberi et al. "Differences in fibronectin-dependence of migrating cell populations" *J Embyol* 187:17–26, 1993; Chin and Werb "Matrix metalloproteinases regulate morphogenesis, migration and remodeling of epithelium, tongue skeletal muscle and cartilage in the mandibular arch" *Development* 124:1519–1530, 1997). This suggests that at least some of the mechanisms regulating myoblast migration may be conserved across developmental stages and into the adult animal, although, as seen in the present work, species differences will require the empirical determination of the combination necessary for any particular species.

DETAILED DESCRIPTION OF PREFERRED EMBODIMENTS

Generally, the nomenclature used hereafter and the laboratory procedures in cell culture, molecular genetics and nucleic acid chemistry and hybridization described below are those well known and commonly employed in the art. Standard techniques are used for recombinant nucleic acid methods, polynucleotide synthesis and microbial culture and transformation (e.g. electroporation and lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y.).

The present invention contemplates assays for detecting the ability of agents to inhibit or enhance myoblast migration and invasion where high-throughput screening formats are employed together with large agent banks (e.g. compound libraries, peptide libraries and the like) to identify antagonists or agonists. Such myoblast migration and invasion antagonists and agonists may be further developed as potential therapeutics and diagnostic or prognostic tools for diverse types of acquired and hereditary degenerative muscle diseases.

1. Screens to Identify Agonists and Antagonists of Myoblast Migration and Invasion A. In vitro Assays There are several different approaches contemplated by the present invention to screen for small molecules that specifically inhibit or enhance the ability of myoblasts to migrate and invade tissue. One approach is to culture the myoblasts in the presence of the compound using standard culture procedures, and then assay for the mobility and invasiveness using assays known to those practiced in the art. The present invention would serve as a positive control and untreated or bovine serum albumin (BSA) treated cultures would serve as a negative control. Another approach would be to detect the expression of proteases suspected to be instrumental for the migration and invasion of myoblasts. After culturing as described above, MMP expression would be detected by zymogen assay, known to those practiced in the art. Furthermore, MMP expression could be detected by Northern or Western blotting. Further still, increased expression of other proteins or molecules induced by the culture conditions could also be determined.

Transfection assays allow for a great deal of flexibility in assay development. The wide range of commercially available transfection vectors will permit the expression of the MMPs. In one embodiment, cells are transiently transfected with an expression construct comprising nucleic acid encoding MMP-1 or MMP-2 that may include (in operable combination) an inducible promotor allowing for the expression of a metalloprotease to levels higher than in the untransfected cells. Increased expression of these metalloproteases may enhance migration and invasion of myoblasts in combination with the compounds to be screened. Cells can be exposed to the agent suspected of modulating myoblast migration and invasion, MMP expression would be turned on, if necessary, and migration and invasion can be measured by techniques known to those practiced in the art. The compositions of the present invention would be used as positive controls. Rates of migration and invasion of cells exposed to the compounds to be screened are compared to rates of migration and invasion of the cells exposed to the compounds of the invention. Transfection with a control expression vector (e.g. an empty expression vector) would serve to compare the effect of MMP over expression on migration and invasion. Rates of migration and invasion can be quantitated by any of a number of ways reported in the literature and known to those practiced in the art.

In another embodiment, stably transfected cell lines expressing MMP-1 or MMP-2 are produced as stocks for further assays. The use of an inducible promoter may be utilized in these systems. Screening assays for compounds suspected of modulating myoblast migration and invasion would be conducted in the same manner as with the transient transfection assays. Using stably transfected cell lines would allow for greater consistency between experiments and allow for inter-experimental comparisons.

B. In vivo Assays

In one embodiment cells will be transfected with a vector that expresses a protein suitable for use as a marker of migration and invasion (e.g. GFP, luciferase or β-gal). The cells will then be cultured with either 1) the compound suspected of being agonistic or antagonistic for myoblast migration and invasion, 2) a negative control or 3) positive control comprising the present invention. After culturing, at least a portion of the cells from each condition will be introduced into patients or laboratory animals. Myoblasts may be reintroduced into the patients, if necessary. After a suitable length of time muscle biopsies will be taken and assayed for migration and invasion by detecting cells that express the marker protein.

In another embodiment, compounds suspected of modulating myoblast migration and invasion may be given directly to the patient. Administration may be oral, intravenous, intraperitoneal, intramuscular or by other means as appropriate for the compound being administered. The suspected compound may be administered prior to, during or after introduction of the myoblasts into the patient. The myoblasts may be cultured with or without the compound suspected of modulating myoblast migration and invasion. The myoblasts will then be introduced into the patient. The suspected compound, as well as the cultured myoblasts, may be reintroduced into the patient, if necessary. Migration of the myoblasts will then be assayed as described herein above.

2. Methods of Treatment of Degenerative Muscle Diseases

The present invention demonstrates that cultured myoblasts can be induced to migrate and invade muscle tissue. Once there, the introduced myoblasts fuse to existing myofibrils. This technology may be used in the treatment of degenerative muscle diseases. In one embodiment, myoblasts are obtained from an immunocompatible donor or from the patient. The myoblasts are cultured with bFGF and FN, as described herein. Thereafter, at least a portion of the myoblasts are introduced into the patient. Reintroduction of myoblasts is also contemplated in this invention. In another embodiment, myoblasts would be transfected with a marker protein (e.g. GFP, luciferase or β-gal), prior to culturing with bFGF and FN, to permit the monitoring of the migration and invasion of the myoblasts. In yet another embodiment the myoblasts would be transfected with MMP-1 or MMP-2, prior to culturing with bFGF and FN, to permit enhanced migration and invasion.

3. Methods Related to Gene Therapy

The present invention demonstrates that cultured myoblasts can be induced to express peptides from transfected expression constructs. Additionally, the present invention demonstrates that cultured myoblasts can be induced to migrate and invade muscle tissue. This technology may be used in the delivery of therapeutic gene products thereby allowing for an effective method of gene therapy. In one embodiment, the myoblasts are obtained from an immunocompatable donor or from the patient. The myoblasts are transfected with the construct able to express the protein of interest. The myoblasts are then cultured with bFGF and FN, as described herein. Thereafter, at least a portion of the myoblasts would be introduced into the patient. In another embodiment myoblasts would be transfected with a marker protein (e.g. GFP, luciferase or β-gal), prior to culturing with bFGF and FN, to permit the monitoring of the migration and invasion of the myoblasts. In yet another embodiment the myoblasts would be transfected with MMP-1 or MMP-2, prior to culturing with bFGF and FN, to permit.enhanced migration and invasion. The latter embodiment, therefore, comprises myoblasts transfected with a first vector encoding a therapeutic gene product and a second vector encoding a metalloprotease gene.

Experimental

The following examples are intended to illustrate, but not limit, the present invention.

Materials and Methods

Cell Culture

Mouse myoblasts were previously isolated from hind limb muscles of 4–6 week old severe combined immunodeficient (SCID) mice and clonally purified from contaminating fibroblasts (Yao et al. "Primary myoblast-mediated gene: transfer: persistent expression of human factor IX in mice" *Gene Therapy* 1:99–107, 1994). Myoblasts (approximately $1 \times 10^6$ cells) were plated on 6 cm tissue culture plates coated with 0.5% gelatin (Sigma, St. Louis, Mo.) and grown in growth medium consisting of Dulbecco's Modified Eagle Medium (DMEM) (Gibco BRL, Gaithersburg Md.) supplemented with 20% fetal bovine serum (FBS; Gibco) and 0.5% chick embryo extract (CEE; Gibco). All animal studies were carried out following the institutional guidelines for ethical animal use. Human myoblasts were isolated using trypsin digestion from abdominal wall or chest wall muscle biopsies, and surgery. Written consent was obtained from all patients prior to biopsy isolation as approved by the University Hospital's Institutional Regulation Board on the use of human subjects. Cells were preplated on uncoated plates for 1 hour to separate muscle fibroblasts. Approximately 95% of the cells were desmin-positive following immunohistochemical staining of representative culture samples, and were capable of differentiation into myotubes, indicating high purity of the myoblast preparation. All experiments were done with myoblasts of passage 7 or lower.

In Vitro Migration and Invasion Assays

Myoblast migration and invasion were examined using a commercially available in vitro cell migration and invasion assay kit (Biocoat, Becton Dickinson, Franklin Lakes, N.J.) as described by Albini et al. (A rapid in vitro assay for quantitating the invasive potential of tumor cells *Cancer Res* 47:3239–3245, 1987). Myoblasts were grown to approximately 70% confluence, rinsed three times in serum-free DMEM, followed by incubation for 3 hours in 0.2% bovine serum albumin (BSA) in DMEM to eliminate the effects of serum. Cells were then trypsinized and collected by centrifugation. Cells were resuspended in serum-free DMEM at a density of $1 \times 10^5$ cells/ml, and 0.5 ml aliquots of cell suspension were added to the top chamber. The following stimuli, which were obtained from R&D (Minneapolis, Minn.) unless otherwise noted, were used: bovine basic fibroblast growth factor (bFGF), recombinant human tumor necrosis factor-α (TNF-α) (Sigma), purified human transforming growth factor-β1 (TGF-β1), recombinant human platelet-derived growth factor-BB (PDGF-BB), recombinant human insulin-like growth factor-I (IGF-I), recombinant hepatocyte growth factor (HGF); and human serum fibronectin (Sigma). Fibronectin subfragments of 45 KDa (Sigma), 120 kDa (Gibco), 63 kDa (Retronectin, Takara) and 70 KDa (Sigma) were used alone or in combination. The growth factor concentrations used were those which could produce maximal effects as examined in the present studies by extending from values reported by Bischoff ("Chemotaxis of skeletal muscle satellite cells" *Devel. Dynamics* 208:505–515, 1997). For migration studies, the upper chamber membrane was coated with 0.1% gelatin and cells were allowed to migrate for 8–12 hours, while for invasion studies, the upper membrane was coated with 5 µl of MATRIGEL® diluted to 5 mg/ml in sterile phosphate buffered saline (PBS) and cells were allowed to invade for 24 hours. The top side of the insert membrane was scrubbed free of cells using a cotton swab and the bottom side was stained using the Leukostat-I system (Fisher Diagnostics, Pittsburgh, Pa.). The number of cells per field was counted in 10 randomly selected fields and averaged for each condition.

To evaluate the effects of inactivation or activation of MMPs, aliquots (0.05 units in 50 µl PBS) of purified human plasmin (Sigma) or 50 mM N-acetyl cysteine (NAC; Sigma) were added with the cells to the top chamber of the migration assay and growth factor was added to the bottom. Plasmin is known to activate MMPs, (Reich et al. "Effects of inhibitors of plasminogen activator, serine proteinases and collagenase IV on the invasion of basement membranes by metastatic cells" *Somatic Cell Mol. Genetics* 18:247–258, 1988) while NAC is a general inhibitor for gelatinase, such as MMP-2 (gelatinase A) and MMP-9 (gelatinase B), and less strongly inhibits collagenases such as MMP-1 (Albini et al. "Inhibition of invasion, gelatinase activity, tumor take and metastasis of malignant cells by N-acetylcysteine" *Int. J. Cancer* 61:121–129, 1995).

Gelatin Zymography

Gelatin zymography for assaying MMPs was carried out as previously described (Guerin and Holland "Synthesis and secretion of matrix-degrading metalloproteinases by human skeletal muscle satellite cells" *Devel. Dynamics* 202:91–99, 1995) with minor modifications. Briefly, myoblasts were grown in 6 cm tissue culture plates to approximately 70% confluence, then rinsed three times with serum-free DMEM and incubated for 3 hours in DMEM containing 0.2% BSA to eliminate the effects of serum. Growth factors were added and cells were incubated for 24 hours. Culture medium was then collected, centrifuged to pellet detached cells, and concentrated ten- to twenty-fold using the Centricon-10 (Amicon, Beverly, Mass.) system. The protein concentration of the supernatants was determined using the Bio-Rad protein microassay system with BSA used as the standard. Samples were stored at −70° C. until use. For gelatin zymography, aliquots (10 μg as the total protein per sample) were electrophoresed at constant voltage on a 10% polyacrylamide gel containing 2 mg/ml gelatin. The gel was rinsed three times for 15 min in 2.5% Triton-X 100 to remove SDS and renature the proteins, then incubated in MMP activation buffer (0.05 M Tris-HCl, pH 7.5 with 5 mM $CaCl_2$) for 24 hours at 37° C. with constant shaking. Gels were stained overnight in 0.5% Coomassie blue R-250, and destained for 1 hour in 40% methanol:10% acetic acid. Proteinase activity was quantified by densitometric scanning of bands using a Bio-Rad Gel Doc 1000 video camera imaging system (Bio Rad, Hercules, Calif.).

Construction of MMP Expression Vectors

Expression vectors containing human MMP genes were generated with the plasmid pNGVL3, which contains the cytomegalovirus (CMV) immediate-early enhancer, 5' untranslated region and intron, the rabbit β-globin poly(A) signal sequence and a kanamycin resistance marker. This plasmid vector was obtained from the Vector Center of the University of Michigan. The MMP-9 coding cDNA insert was excised from the vector PBS-92 with Xba I, and ligated into pNGVL3 at the Xba I site with T4 DNA ligase (Boehringer Mannheim, Indianapolis, Ind.), generating pNGVL3/MMP-9. Competent bacteria (Top 10; Invitrogen, La Jolla, Calif.) were transformed and kanamycin-resistant colonies were selected.

PNGVL3/MMP-2 was prepared by removing the MMP-2 cDNA from the PBS-GEL plasmid vector by Not I/Eco RI digestion and ligating into pNGVL3 at the Not I/Eco RI sites. Expression vector pNGVL3/MMP-1 was prepared by inserting the MMP-1 cDNA isolated from pcD-X into pNGVL3 at the Sal I site. PBS-92 and PBS-GEL were kindly provided by Dr. Gregory Goldberg of Washington University School of Medicine, while pcD-X was obtained from ATCC. All constructs were examined by restriction mapping to confirm the correct structures and orientations.

Transient Transfection, Zymography and Migration/Invasion Assays

Transient over-expression of individual MMPs was carried out as follows. Myoblasts grown in growth medium to approximately 50% confluence in 6 well plates were transfected overnight by adding growth medium containing 1 μg expression vector DNA and 3 μl FUGENE 6® reagent according to the manufacturer's instructions (Boehringer Mannheim, Indianapolis, Ind.). Under similar conditions using pCH110 vector DNA (β-galactosidase expression plasmid), approximately 20–25% of mouse myoblasts could consistently be transfected. For co-transfection with MMP-1 and MMP-2 vectors, a total of 2 μg of vector DNAs composed of 1 μg of each expression vectors, were mixed with 6 μl of FUGENE6® for transfection. The following morning (12–14 hrs incubation), the transfection mixture was removed and the cells harvested for cell migration/invasion assays as described above except 10 μg/ml of fibronectin (10% of the regular concentration) was added to the bottom chamber to prime cell migration and invasion. The effects of NAC and plasmin on the transfected cells were assayed as described above. Zymography analysis of the culture medium of transfected cells was carried out as described above.

Northern Blot Analysis

Northern blot analysis of transiently transfected cells was carried out according to the standard method. Briefly, myoblasts were grown in 10-cm culture dishes to approximately 50% confluence, and were transfected with a mixture of 33 μl Fugene 6® (Boehringer Mannheim) and 11 μg MMP expression vector DNA according to the manufacture's instructions. After 36 hours, cells were harvested and total cellular RNA was isolated using the TRIzol total RNA isolation kit (GIBCO-BRL). Agarose gel electrophoresis was then carried out using 20 μg of the RNA preparation for each lane and the cDNA fragment for each MMP labeled with $^{32}P$ to $1\times10^9$ cpm/μg as specific probes for each MMPs. Filters were separately hybridized with each probe, washed and exposed to an X-ray film (Kodak, Rochester, N.Y.). Filters were rehybridized with an internal control probe, $^{32}P$-labeled RNR18 (18S ribosomal RNA cDNA) to confirm equal RNA loading to the lanes.

Myoblast Implantation In Vivo

All animal studies were carried out following the institutional guideline for animal use. For in vivo studies, SCID mouse myoblasts transduced with a BAG retrovirus containing the beta-galactosidase (β-GAL) reporter gene and selected as previously described (Yao and Kurachi "Implanted myoblasts not only fuse with myofibers but also survive as muscle precursor cells" *J. Cell Sci* 105:957–963, 1993), were grown in growth medium on 15 cm plates. When cells reached 70% confluence they were harvested by trypsinization using standard methods, rinsed twice in phosphate buffered saline (PBS), and resuspended in DMEM containing either bFGF (1 μg/ml), fibronectin (50 μg/ml) or both, at a concentration of $2\times10^7$ cells/ml. Mice at 2.5 months of age were anesthetized with Metofane (Mallinckrodt Veterinary, Mundelein, Ill.) and the skin overlying the vastus musculature of the lower leg was exposed under aseptic conditions. Aliquots of cells ($1\times10^6$ in 50 μl total solution) were injected into the midbelly of the vastus (thigh) musculature; the muscle was held closed with forceps for several seconds to avoid leakage of cell solution out of the muscle, and the skin was closed using surgical staples. Three weeks after cell implantation, animals were sacrificed and the vastus musculature was surgically removed, frozen in isopentane cooled in liquid nitrogen, and stored at −70° C. until use. Transverse muscle sections (10 μm) were cut through the midbelly of the muscle group by the Morphology Core facility of this Medical School.

Muscle sections were stained for β-GAL activity using the standard histochemical staining procedure (Rando et al.

"The fate of myoblasts following transplant into mature muscle" *Exper. Cell Res.* 220:383–389, 1995). Briefly, sections were fixed for 10 minutes in 2% formaldehyde in PBS then rinsed three times with PBS. Sections were incubated in X-GAL reaction medium (1 mg/ml 5 bromo-4 chloro-3 indolyl β D-galactopyrano-side, 5 mM $K_3$ Fe(CN)$_6$, 5 mM $K_4$Fe(CN)$_6$, 2 mM $MgCl_2$ in PBS) for 18 h at 32° C. The total number of β-GAL-positive fibers (stained blue) per section was counted for 5 different sections spanning the entire injection site for each animal and averaged. For some animals, double staining of sections for the β-GAL activity and laminin immunohistochemistry was done to determine the localization of the β-GAL positive cells relative to the connective tissue. Sections were first immunohistochemically stained for laminin using polyclonal anti-laminin antibodies (Sigma) diluted 1:40 in PBS. Immunostaining was visualized using a horseradish peroxidase (HRP) enzyme immunostaining kit (Histostain; Zymed laboratories, San Francisco, Calif.). Sections were then fixed in formaldehyde and stained for β-GAL as described above.

EXAMPLE I
Mouse Myoblast Migration and Invasion in vitro

All of the growth factors (bFGF, TNF-α, PDGF-BB, TGF-β1, IGF-I, HGF) and fibronectin tested in vitro stimulated migration of mouse myoblasts to various degrees. Results are shown in FIG. 1. Myoblasts ($5 \times 10^4$ cells/well) were stimulated with various growth factors and fibronectin, and their ability to migrate or invade through a MATRIGEL® barrier (panel a, mouse myoblast migration at 12 hours; panel b, mouse myoblast invasion at 24 hours). Stimulants were used at the following final concentrations: 100 ng/ml TNF-α; 25 ng/ml bFGF at; 50 µg/ml human serum fibrone ctin (Fn); 20 ng/ml PDGF-BB; 2 ng/ml TGF-β1; 100 ng/ml IGF-I; 10 ng/ml HGF. Bars represent mean±SEM from a minimum of 3 separate experiments. The largest individual effects were seen in response to fibronectin and bFGF stimulation (14 and 12-fold over the DMEM control, respectively), while HGF and TGF-β1 had smaller, but significant effects (8 and 5-fold, respectively). The combination of bFGF and fibronectin produced an additive effect, stimulating migration >27-fold over the DMEM control. Unexpectedly, none of the fibronectin subfragments, which contain all known binding sites for cells, heparin, and collagen, showed effects on invasion and migration either alone or in combination (data not shown).

Further studies were done to elucidate the role of MMPs in cytokine-mediated mouse myoblast migration. Myoblast migration was assayed as described for FIG. 1 except 0.05 units/ml of purified human plasmin or final 50 mM NAC was added to the top chamber with the cells at the start of the assay (FIG. 2, panels a and c (at 12 hours), mouse myoblast migration assays with various stimulants as labeled; panels b and d (at 24 hours), mouse myoblast invasion assays with various stimulants as labeled). Bars represent mean±SEM from 4 separate experiments. Treatment of cells with both bFGF and plasmin, which is a proteolytic activator of MMPs (Reich et al. "Effects of inhibitors of plasminogen activator, serine proteinases and collagenase IV on the invasion of basement membranes by metastatic cells" *Cancer Research* 48:3307–3312, 1988), increased the migrational response to bFGF by nearly twofold. Unexpectedly, treatment with plasmin alone had a slightly negative effect on myoblast migration compared to the control (FIG. 2a). N-acetylcysteine (NAC), an inhibitor of gelatinases such as MMP-2 and MMP-9 (Albini et al. "Inhibition of invasion, gelatinase activity, tumor take and metastasis of malignant cells by N-acetylcysteine" *Int. J. Cancer* 61:121–129, 1995), efficiently reduced the effect of bFGF on mouse myoblast migration to a level similar to the BSA control. Moreover, addition of NAC resulted in a dramatic reduction of the effect seen by a combination of bFGF and plasmin, suggesting that the stimulatory effect of plasmin is likely attributable to proteolytic activation of gelatinases, and is not due to a direct effect of plasmin on cell migration (FIG. 2a). As expected, NAC attenuated the effects of treatment with bFGF and fibronectin in combination (FIG. 2c). Plasmin also attenuated the effect of this combination, presumably because of proteolytic fragmentation of fibronectin by plasmin. These results demonstrated the important role of a gelatinase(s) and its activation in the effects conferred by bFGF, fibronectin or their combination on migration of mouse myoblasts.

The same set of growth factors also stimulated MATRIGEL® invasion to various degrees (FIG. 1b). Basic FGF again had the largest effect on mouse myoblast invasion across a MATRIGEL® barrier, increasing it by approximately 7-fold over the control, while fibronectin gave a 4-fold increase. The combination of bFGF and fibronectin gave >8-fold higher invasion activity over the BSA control. As observed for migration, plasmin further increased the effects of bFGF, and NAC treatment drastically reduced such stimulatory effects to the control levels, supporting the important role of a gelatinase(s) and its activation on myoblast invasion (FIG. 2b). Addition of plasmin, however, lowered the greatly enhanced effects obtained by a combination of bFGF and fibronectin together (FIG. 2d), agreeing with its effect observed on migration.

EXAMPLE II
Zymography Analysis of Mouse Myoblasts

Figure 3:
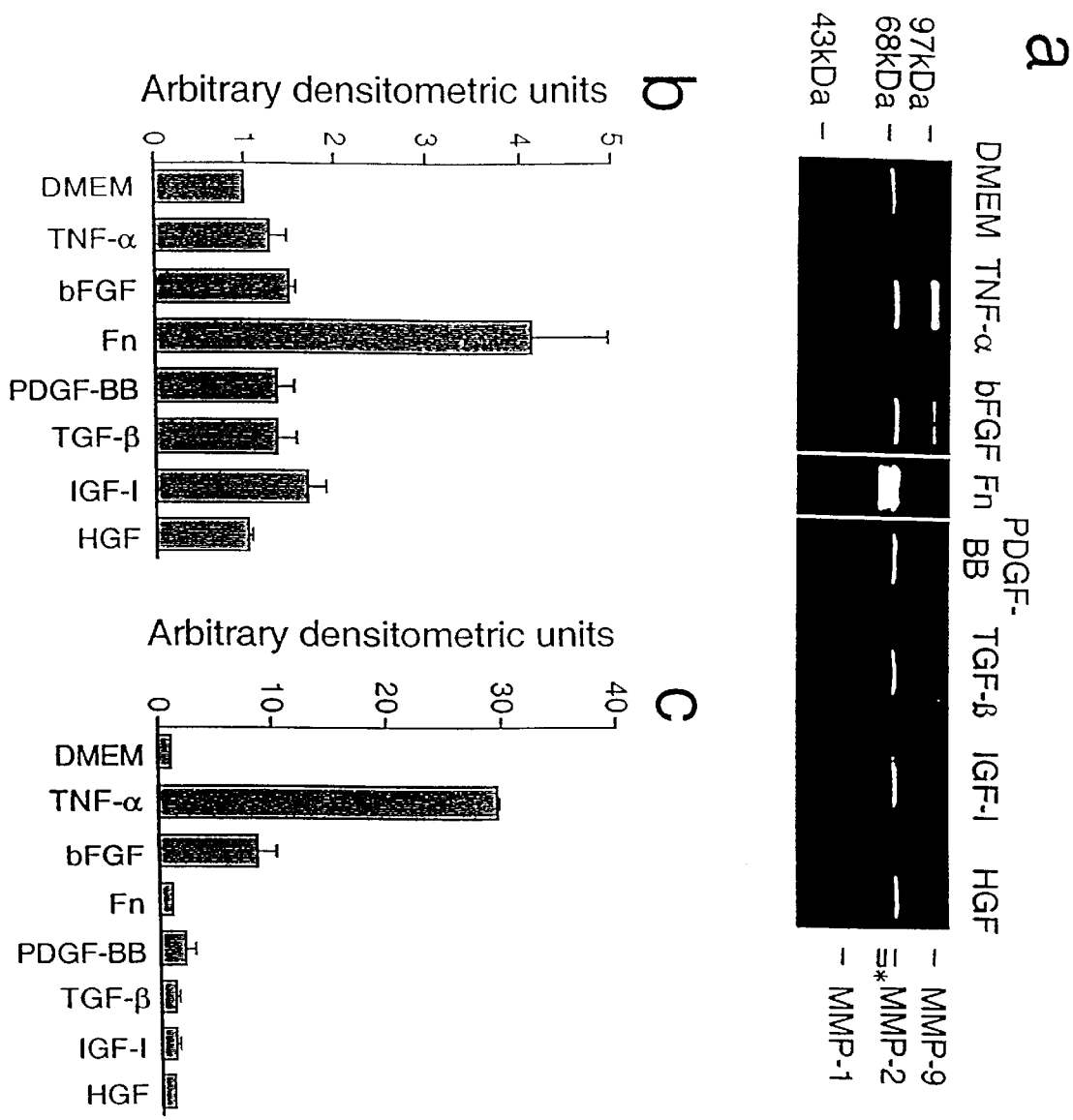
FIG. 3 shows a gelatin zymogram for MMP expression by mouse myoblasts. Panel a, gelatin zymogram of culture medium samples following treatment of cells with various growth factors for 24 hours; panels b and c, quantification of the zymograms for MMP-2 and MMP-9, respectively.

The effects of growth factors and fibronectin on MMP expression by mouse myoblasts are shown in FIG. 3a. Mouse myoblasts grown in serum-free medium constitutively expressed MMP-2 (zymogen form, 72kDa), which still appears as a zymogram band due to its inherent gelatinase activity (Reich et al. "Effects of inhibitors of plasminogen activator, serine proteinases and collagenase IV on the invasion of basement membranes by metastatic cells" *Cancer Research* 48:3307–3312, 1998) (FIG. 3). Proteolytic degradation of gelatin due to MMPs appears as clear bands against the dark background. Bands marked with an asterisk (64 and 62 kDa) indicate the activated forms of MMP-2. The lane for fibronectin treatment was run simultaneously on a separate gel, and the scanned picture is placed in the order for comparison. Treatment of mouse myoblasts with bFGF, PDGF-BB, TGF-β and IGF-I had modest but consistent effects on total MMP-2 expression, increasing its expression by 49%, 35%, 36%, and 69%, respectively (FIG. 3b), while TNF-α and bFGF also greatly increased MMP-9 expression (110 kDa band) to approximately 30- and 10-fold over the DMEM control level, respectively (FIG. 3c). Values are arbitrary densitometric units, which are normalized to DMEM control for each experiment and shown as values±SEM representing a minimum of 3 experiments per condition. The subfragment of 120 kDa showed some MMP-2 activation, but only at a very low, insignificant level (not apparent in this Figure). Using gelatin zymography, MMP-1 expression (57 kDa) was not detected with or without growth factor treatment, although this does not exclude the possibility of its low level induction, which may have been below the limit of detection of the gelatin zymography system.

Treatment of mouse myoblasts with soluble plasma fibronectin resulted not only in increased MMP-2 expression by approximately 2-fold, but also its substantial proteolytic conversion to the activated and intermediate forms migrating as a doublet at 64 and 62 kDa, respectively (FIG. 3a). This effect was specific for soluble fibronectin, because cells grown on a fibronectin-coated substrate showed only constitutive expression of MMP-2 without any apparent proteolytic activation (DMEM control) (FIG. 3).

Most fibronectin subfragments of various sizes, essentially covering almost all domains of the molecule (the amino terminal small region not included in the test samples), neither increase MMP-2 expression nor its activation when used either separately or in combination. Mouse myoblasts were treated for 24 hours with either DMEM alone, fibronectin (50 µg/ml), or individual fragments (37.5 µg/ml) of 45, 120, 63 (Retronectin), 75 kDa and their combinations, 45 kDa/120 kDa and 120 kDa/63 kDa. These results suggest that either the responsible regions of the fibronectin molecule are not contained within these fragments, or that physical linkage of some or all of these fragments may be needed for conferring optimal induction of MMP-2 activation. This data is shown in FIG. 4. MMP-1, MMP-2 and MMP-9 positions are shown on the right side. Bracket with asterisk indicates the 64 and 62 kDa activated forms of MMP-2, which are very prominent for the fibronectin-treated lane and at very low levels in lanes with 120 kDa fragment (even hard to see in the picture). Subfragment of 120 kDa, known to contain cell adhesion modules, showed MMP-2 activation activity, but at an extremely low level (not obvious in FIG. 4). Apparent sizes of MMPs observed in the present study agree with those previously reported by others (Aimes et al. "Cloning of a 72 kDa matrix metalloproteinase (gelatinase) from chicken embryo fibroblasts using gene family PCR: expression of the gelatinase increases upon malignant transformation" *Biochem. J.* 300:729–736, 1994; Masure et al. "Mouse gelatinase B: cDNA cloning, regulation of expression and glycosylation in WEHI-3 macrophages and gene organization" *Eur. J. Biochem.* 218:129–141, 1997; Chen et al. "Isolation and characterization of a 70-kDa metalloproteinase (gelatinase) that is elevated in Rous Sarcoma virus-transformed chicken embryo fibroblasts" *J. Biol. Chem.* 266:5113–5121, 1991).

EXAMPLE III

MMP Over-expression and Mouse Myoblast Migration and Invasion

Transient over-expression of MMP-1, MMP-2, and MMP-9 was tested in myoblasts to determine whether expression of individual MMPs was sufficient to produce increased migration and/or invasion. Transient transfection rather than stable transduction was used, because secretion of over-expressed MMPs by transfected cells (approximately 20–25% of the cells) should be sufficient to allow most, if not all, cells access to increased levels of secreted MMPs and avoid prolonged exposure of cells to over-expressed MMPs. Successful transfection of MMP-1, MMP-2 and MMP-9 were confirmed by gelatin zymography, showing dramatically increased intensity of bands of approximately 57, 72 and 92 kDa (human MMP-9 is smaller than the mouse counterpart), respectively (FIG. 5a), and by Northern blot analyses (FIG. 5b, c, and d) of the transfected cells. The high molecular weight bands within the bracketed region marked with + presumably represent complexes of the over-expressed MMP with metalloproteinase inhibitors. Gelatin zymography of the culture medium of cells transfected with the MMP-1 vector showed a substantial induction of MMP-1 expression from non-detectable levels in control (FIG. 5a). Though gelatin zymography is not optimal for demonstrating MMP-1 activity, the presence of elevated MMP-1 levels is clearly seen as a doublet (zymogen and activated form) migrating near 55–57 kDA. Expression levels of MMP-2 and MMP-9 in transfected cells, as assayed by zymography, were increased by >3.5- and 10-fold, respectively, over cells transfected with the control vector, pNGVL3 (FIG. 5a).

Overexpression of each MMP did not significantly affect the expression levels of the other two MMPs. Northern blot analysis further confirmed the elevation in mRNA levels for each MMPs (FIG. 5b, c and d). Lanes 1, 2 and 3 are for cells transfected with DMEM (control), pNGVL3 with no MMP inserts and pNGVL3 with MMP inserts, respectively, as indicated. Panels b, c and d are for MMP-1, MMP-2 and MMP-9, respectively. Positions for 28S and 18S RNAs are shown on the left, and those of MMP mRNA bands are shown on the right by arrows. MMP-9 has two mRNA bands. Because of the high level expression of MMPs for lanes 3, intrinsic MMP mRNA bands in lane 1 and 2 are not yet visible at this film exposure time. The presence of equal amount of total RNA in each lane is shown in the lower panels for the internal control RNA, RNR18 (18S ribosomal RNA cDNA).

Transfection of mouse myoblasts with MMP-1 or MMP-2 increased the migration of mouse myoblasts by 2.6- and 1.6-fold, respectively, over myoblasts transfected by the control plasmid vector (FIG. 6a), and invasion capability by 2-fold for both MMP-1 and MMP-2 (FIG. 6b). Transfection with MMP-9 had only marginal effects on both migration (FIG. 6a) or invasion (FIG. 6b) of mouse myoblasts. In FIG. 6a, cells transfected with each expression vector were examined for their migration capability by assaying for 2 hours in the presence of BSA or a low level fibronectin (FN) (10 µg/ml) to prime cell migration. In FIG. 6b the conditions used are similar to those for migration, except invasion was allowed to proceed for 6 hours.

NAC treatment decreased the migration capability of both MMP-1 and MMP-2 over-expressing myoblasts to 35% and 22% (n=4) of that of non-NAC treated cells, respectively. NAC also decreased the invasion of myoblasts over-expressing MMP-1 and MMP-2 to 40% and 28% (n=4) of the non-treated cells, respectively. These results further supported the involvement of MMP-1 and MMP-2 in myoblast migration and invasion. Co-transfection of MMP-1 and MMP-2 gave only 92.6% or 86% migration activity obtained by individual transfection of MMP-1 or MMP-2, respectively, demonstrating the competitive nature of their action with respect to conferring stimulatory effects on migration. The increased amount of FUGENE 6® used for the double transfections did not show any significant adverse effects on cell growth or morphology, eliminating the possibility of adverse effects of the transfection procedure. In these experiments, myoblast cell number as well as myotube number after differentiation were not significantly different between MMP-transfected and untransfected cells, indicating that MMP over-expression had little effect on myoblast proliferation and differentiation under the experimental conditions used (data not shown).

These results suggest that over-expression of MMP-2 and MMP-1, but not MMP-9, can facilitate myoblast migration and invasion in vitro. In each panel the bars represent mean±SEM from three individual experiments.

EXAMPLE IV

Human Myoblast Migration, Invasion and MMP Expression

The effects of growth factors on human myoblast migration in vitro (12 hour time point) were somewhat different from those observed with mouse myoblasts. All the growth factors tested showed substantial stimulatory effects over the BSA control, ranging from 20–100-fold. The greatly elevated level of migration of human myoblasts was due in part to the extremely low migration in the BSA control (basal level) of human cells compared to mouse cells. The largest effects on human myoblast migration were produced by fibronectin (100-fold), PDGF (about 62-fold), TGF-β (about 54-fold) and HGF (46-fold) over the control level, while bFGF produced only a 37-fold stimulation (FIG. 7a). Moreover, unlike mouse myoblasts, the combination of fibronectin and bFGF produced approximately the same effects as fibronectin alone. These effects were significantly increased by plasmin treatment, and greatly reduced by NAC (FIG. 7c), indicating the critical involvement of gelatinase activity.

The effects of growth factors on human myoblast invasion of MATRIGEL® are shown in FIG. 7b (24 hour time point). All growth factors produced lower effects on human cells compared to mouse cells, while fibronectin alone or fibronectin/bFGF combination still produced a 2.3-fold or 6-fold stimulation, respectively, over the BSA control (FIG. 7d).

Figure 8:
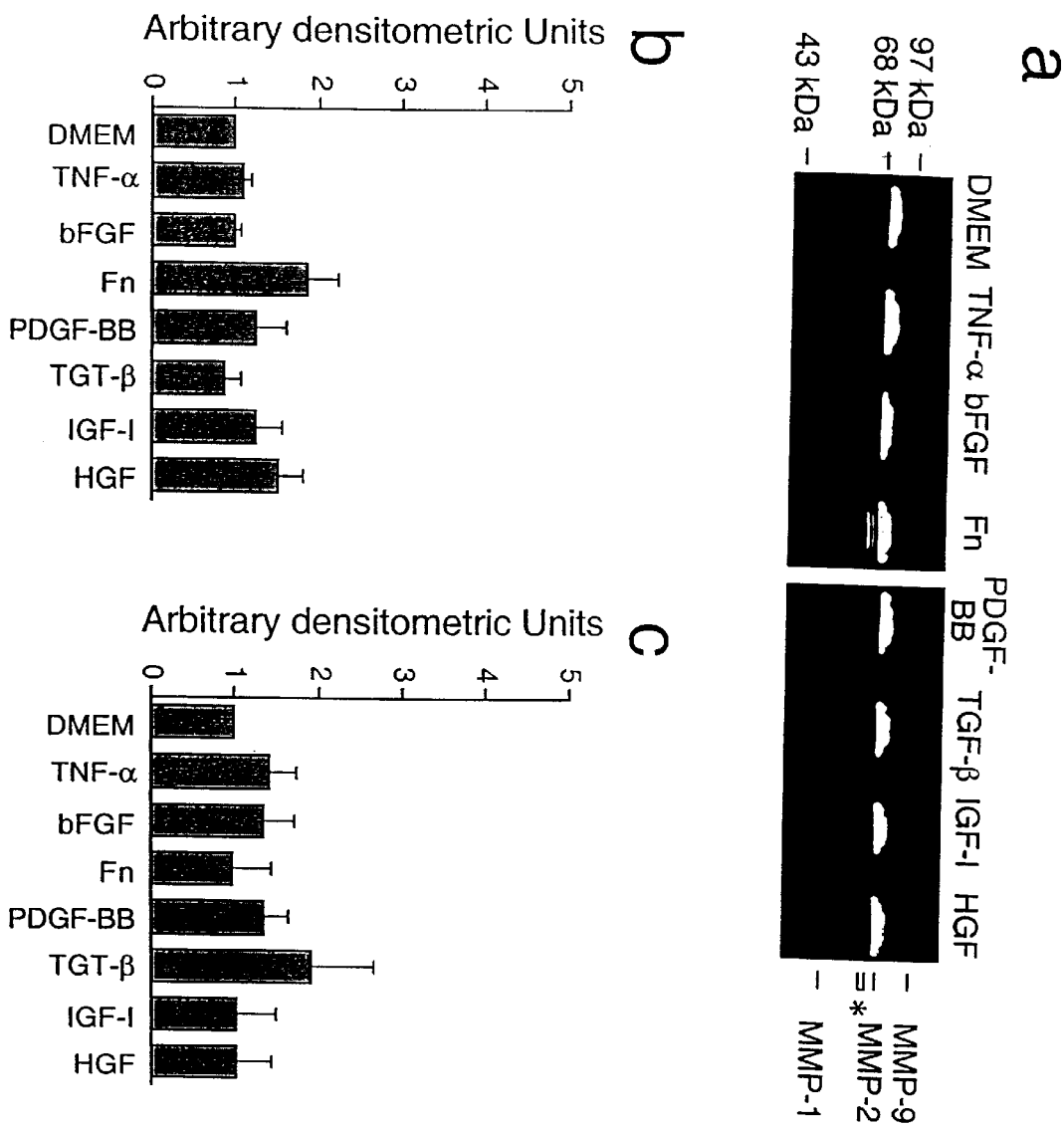
FIG. 8 shows a gelatin zymogram of human myoblasts treated with various stimulants. Similar conditions described for mouse myoblasts (FIG. 3) were used. Panel a, zymogram for control cells and cells transfected with MMP expression vectors; panel b, relative levels of MMP-2 compared to the DMEM control panel c, relative level of MMP-9 compared to the DMEM control. Activated forms of MMP-2 are shown by bracket with asterisk.

Human myoblasts showed a higher basal level of MMP-2 expression than that of mouse myoblasts. This level was approximately 3-fold higher than the basal MMP-2 expression level of mouse myoblasts (data not shown), thereby possibly explaining, in part, the higher migration rate. MMP-2 expression (72 kDa band), as assayed by zymography, was not significantly affected by any of the growth factors tested, while stimulation by intact fibronectin produced a significant increase in MMP-2 activation, similar to that observed in mouse cells (FIG. 8a and b). Unlike mouse cells, human myoblasts showed only marginal increases in MMP-9 expression (92 kDa band) with TNF-α or bFGF stimulation (FIG. 8c). Both mouse and human myoblasts were used at a similar passage number, and myoblasts from both species were obtained from mature muscle samples (4–6 weeks old for mouse, 8–44 years old for human), suggesting that passage and/or age differences may not account for the discrepancies observed between human and mouse myoblasts. These results strongly suggest that while there are similarities, there are also species-specific differences in basal MMP expression as well as induction of MMPs in response to growth factor stimulation.

EXAMPLE V
Mouse Myoblast Incorporation in vivo

Hindlimb muscles of SCID mice were injected with $5 \times 10^5$ BAG-SCID myoblasts, and analyzed 3 weeks later. Sections prepared from mouse hindlimb muscle injected with SCID mouse myoblasts carrying a β-GAL reporter gene were double stained for laminin (a component of the basal lamina) and for β-GAL, using laminin immunohistochemistry and X-GAL histochemistry, respectively. Myoblasts were able to incorporate into the muscle, resulting in numerous β-GAL-positive myofibers with normal diameters which were scattered throughout the muscle (FIG. 9a). However, myoblasts also remained trapped in areas of connective tissue such as fascicle sheaths, where they fused with one another to form new myotubes (FIG. 9b). In other cases, myoblasts appeared to migrate out of such barriers but were probably forced there due to the injection pressure where they were unable to cross the fiber basal lamina and, thus, remained outside the myofibers, again forming new myotubes (FIG. 9c; some typical representatives are shown by arrow heads). These results supported the hypothesis that the connective tissue structures surrounding fiber bundles and surrounding the fibers themselves may function as a barrier to the incorporation of myoblasts into the adult myofibers in vivo. Sections at 8 μm. The photographs were taken at an original magnification of 200-fold.

EXAMPLE VI
Effects of bFGF and Fibronectin in vivo

Stimulation of myoblasts prior to muscle implantation, with bFGF, fibronectin, or both together, resulted in substantial increases in myoblast incorporation into existing myofibers, as shown by 2.3-, 2-, and 5-fold increases in the number of β-GAL-positive myofibers, respectively, over that of the BSA treated control (FIG. 10). The number of β-GAL positive myofibers were quantified after implantation of BAG-transduced SCID myoblasts treated with DMEM alone (control), 1 μg/ml bFGF, 50 μg/ml fibronectin, or 1 μg/ml bFGF+50 μg/ml fibronectin. Bars indicated mean±SEM for 4 animals. Treatment with bFGF and bFGF+ fibronectin stimulated increased incorporation of implanted myoblasts into myofibers compared to DMEM alone. Tissues were immunostained for visualizing laminin.

Effects of bFGF and fibronectin on myoblast incorporation were further visualized by staining representative sections of the muscle tissues after injection with untreated myoblasts (FIG. 11a, BSA control) or myoblasts treated with bFGF plus β-GAL (FIG. 11b). Representative tissue sections used for analyses in FIG. 10 are shown. Arrows indicate some representative myofiber cells successfully fused with implanted β-GAL-marked myoblast cells. Arrow heads indicate some representative myotubes formed in connective tissues. No counter stain was done for the tissues. These photographs were taken at an original magnification of 100-fold. These results demonstrated that such stimuli can actually augment fusion efficiency of implanted myoblasts with the adult host myofiber cells. These results, however, do not rule out the possible contribution of mechanisms other than increased migration and invasion in the increased myoblast incorporation.

From the above, it is clear that the present invention provides a less destructive approch to myoblast gene transfer. The above-identified composition and methods can be readily employed ex vivo to prepare myoblasts for transfer into humans.

What is claimed is:

1. A composition, comprising isolated myoblasts co-transfected with a gene encoding a metalloprotease and a gene encoding a marker protein to detect cell migration and invasion.

2. The composition of claim 1, wherein said gene encoding a marker protein to detect cell migration and invasion encodes β-galactosidase.

3. The composition of claim 1, wherein said gene encoding a metalloprotease is selected from metalloprotease-1 gene and metalloprotease-2 gene.

4. A method comprising:

a) providing:

i) the composition of claim 1, and ii) a host, b) introducing said composition into said host; and c) detecting said marker protein.

5. The method of claim 4, further comprising providing an agent suspected of being agonistic or antagonistic for myoblast migration and invasion, wherein step b) further comprises introducing said agent into said host.

6. The method of claim 4, further comprising providing at least one growth factor, wherein said co-transfected myoblasts are cultured with said growth factor prior to step b).

7. The method of claim 6, wherein said growth factor is selected from the group consisting of fibroblast growth factor, tumor necrosis factor-α, transforming growth factor-β, platelet-derived growth factor, insulin-like growth factor-I, hepatocyte growth factor, and fibronectin.

8. The method of claim 4, wherein said co-transfected myoblasts comprise myoblasts isolated from said host.

9. The method of claim 4, wherein said co-transfected myoblasts comprise myoblasts isolated from a syngeneic donor.

10. The method of claim 4, wherein said gene encoding a metalloprotease is the metalloprotease-1 gene.

11. The method of claim 4, wherein said gene encoding a metalloprotease is the metalloprotease-2 gene.

12. A composition, comprising a mixture comprising a first population of isolated myoblasts, said first population of myoblasts transfected with a gene encoding a metalloprotease, and a second population of isolated myoblasts, said second population transfected with a gene encoding a marker protein to detect cell migration and invasion.

13. The composition of claim 12, wherein said gene encoding a marker protein to detect cell migration and invasion encodes β-galactosidase.

14. The composition of claim 12, wherein said gene encoding a metalloprotease is selected from metalloprotease-1 gene and metalloprotease-2 gene.

15. A method comprising:
 a) providing:
  i) the composition of claim 12, and
  ii) a host;
 b) introducing said composition into said host; and
 c) detecting said marker protein.

16. The method of claim 15, further comprising providing an agent suspected of being agonistic or antagonistic for myoblast migration and invasion, wherein step b) further comprises introducing said agent into said host.

17. The method of claim 15, further comprising providing at least one growth factor, wherein said co-transfected myoblasts are cultured with said growth factor prior to step b).

18. The method of claim 17, wherein said growth factor is selected from the group consisting of fibroblast growth factor, tumor necrosis factor-α, transforming growth factor-β, platelet-derived growth factor, insulin-like growth factor-I, hepatocyte growth factor, and fibronectin.

19. The method of claim 15, wherein said gene encoding a metalloprotease is the metalloprotease-1 gene.

20. The method of claim 15, wherein said gene encoding a metalloprotease is the metalloprotease-2 gene.

* * * * *